(12) United States Patent
Herman et al.

(10) Patent No.: US 6,171,806 B1
(45) Date of Patent: Jan. 9, 2001

(54) ISOLATED PEPTIDE DEFINED BY SEQ ID NO: 17 AND USES THEREOF

(75) Inventors: Jean Herman; Pierre Coulie; Pierre van der Bruggen; Thierry Boon-Falleur, all of Brussels (BE)

(73) Assignee: Ludwig Institute for Cancer Research, London (GB)

(*) Notice: Under 35 U.S.C. 154(b), the term of this patent shall be extended for 0 days.

(21) Appl. No.: 09/266,294

(22) Filed: Mar. 11, 1999

Related U.S. Application Data

(60) Division of application No. 08/531,864, filed on Sep. 21, 1995, now Pat. No. 5,977,300, which is a continuation-in-part of application No. 08/373,636, filed on Jan. 17, 1995, now Pat. No. 5,997,870, which is a continuation-in-part of application No. 08/253,503, filed on Jun. 3, 1994, now Pat. No. 5,589,334.

(51) Int. Cl.$^7$ ............................. G01N 33/574; C07K 7/06

(52) U.S. Cl. ..................... 435/7.24; 435/7.1; 435/7.21; 435/7.23; 530/328; 436/64

(58) Field of Search ...................... 435/7.24, 7.1, 435/7.21, 7.23; 530/328; 436/64

(56) References Cited

U.S. PATENT DOCUMENTS 5,744,353 * 4/1998 Herman et al. .
6,060,257 * 5/2000 Herman et al. .

* cited by examiner

*Primary Examiner*—Marianne P. Allen
(74) *Attorney, Agent, or Firm*—Fulbright & Jaworski, LLP

(57) ABSTRACT

Tumor rejection antigens presented by HLA-B44 molecules are described. These peptides are useful in diagnostic and therapeutic methodologies. The tumor rejection antigens are not derived from tyrosinase, which has previously been identified as a tumor rejection antigen precursor processed to an antigen presented by HLA-B44.

2 Claims, 14 Drawing Sheets

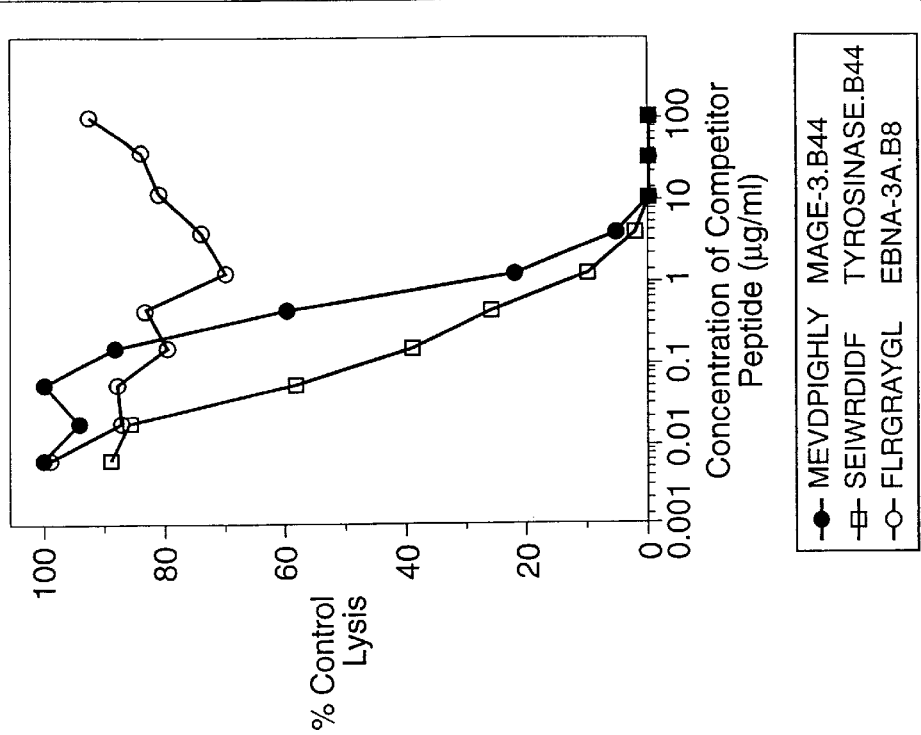
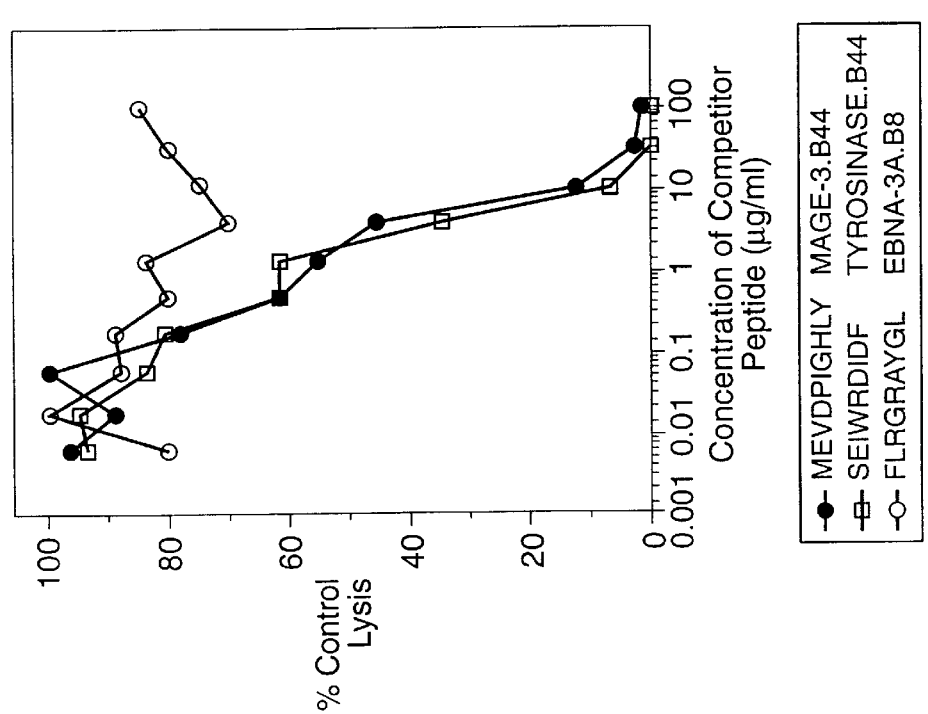

SEQUENCE LISTING (1) GENERAL INFORMATION:

(iii) NUMBER OF SEQUENCES: 27

(2) INFORMATION FOR SEQ ID NO:1:

(i) SEQUENCE CHARACTERISTICS:
      (A) LENGTH: 1896 base pairs
      (B) TYPE: nucleic acid
      (C) STRANDEDNESS: single
      (D) TOPOLOGY: linear (xi) SEQUENCE DESCRIPTION: SEQ ID NO: 1:

```
GCGGCGGTGG CGGAGGCGGA CACATTGGCG TGAGACCTGG GAGTACGTTG TGCCAAATCA      60

TTGCCACTTG CCACATGAGT GTAAATGATG GCGGATGCAA GTATGTCCTC TGCCGATGGG     120

AAAAGCGATT ATGGCCTGCG AAGGTGACAG CCATTATTCT GTAACTTCAG GACTTAGAAA     180

TGACTTTCGG GTGACAAGTA AAATCTTGAT CAGGAGATAC CTAGGATTTG CTTCAGTGAA     240

ATAATTGAGC CAGAACACGG TTGGCACTGA TTCTCGTTCC CCATTTAATG GGGTTTTGGT     300

CTAGTGCTTC CAAGGTTACA CTTCCAGAAA TGTCTTTTTT TTTTCACACT AAAAAAAAAA     360

AAAAGAATCA GCTGTAAAAA GGCATGTAAG GCTGTAACTC AAGGAAAGAT CTGGCAAGCA     420

GCCCTGTGAT AGTAAATTAT GGTCGTGTTC AGGGAATGCT TTCCAGCAAT TCAGTAGACA     480

GTGCTCAGCT GCAATGCAAA AGCCCAGGTC CTTGTCTTTG TCTGCCACTG GCCTCTCATG     540

CCTCAGTTTC CCCATCTGTG AAACAATGGG GATTGGACCA AATATCTGAA ATCCCATGGT     600

TATAGGCCTT CAGGATTACC TGCTGCATTT GTGCTAAAGT TTGCCACTGT TTCTCACTGT     660

CAGCTGTTGT AATAACAAGG ATTTTCTTTT GTTTTAAATG TAGGTTTTGG CCCGAACCGC     720

GACTTCAACA AAAAATAAGA GAAGAAAGGA ATATTTTCTA GCTGTGCAAA TCCTCTCCCT     780

AGAGGAAAAG TTAATTGTTG TGTTGTTTTA ATACTGTTTT TTCCCGTGTA GATTTCTGAT     840

ACTTCAATCC CCTACTCCCC CAAAACAGTT GAAGCCCAGC CCACTCTTAA TGGGCTTATT     900

CACCATTTGT GTAATTCATT AATGCTCATA ATAACCTCAT GAGAAAGCAA CTAGTTTGAT     960

TTTATGTCAG TTTGGAAGCT GAAGATCCAA ACGAGGCATT CTGTGAGATC TATGGAGAGA    1020

TTGGTACAAA CACTGAATAC ATGTAAATTA TACTCAGGGT AGACCCTATT TGTGGTTAAA    1080

ATAGGGATAT TTCCTTTTTT TTTTTTTTTT TTTTGACTGT TTCTTAATCA GTGCCATGCC    1140

AGGAAAATAG GGATGTTTCC TTCCCAGAGA TCTGTGTGTC TTTTTTCAGA AACGTCTGTG    1200

ACAGGCCCAT CAATTTTGAA ATATTTGGTT TTTGAGCCTG TCACTCTAAA CCAGCGTTTA    1260

ACGTTCAAAA GGCAAATAAC TGATGACCAG GCGGCACATT GTTCTGCTCC GTGAGTGTCT    1320

GGCACTGGGA AAGGTGTAGA TTGTCTAGAA TGACAGCAAT TCCGACGCCC CAGTCAGTCC    1380

TGCGTGATTG TGGCGAGGGC GCGTCTGGCA CCGGGAAGGT GTAGATCATC TAGAATGACG    1440
```

```
GCGATTCCGA CGCCCCGGTC AGTCCTGCGT GATTGGCGAG GGTGCATCTG TCGTGAGAAT      1500

TCCCAGTTCT GAAGAGAGCA AGGAGACTGA TCCCGCGTAG TCCAAGGCAT TGGCTCCCCT      1560

GTTGCTCTTC CTTGTGGAGC TCCCCCTGCC CCACTCCCTC CTGCCTGCAT CTTCAGAGCT      1620

GCCTCTGAAG CTCGCTTGGT CCCTAGCTCA CACTTTCCCT GCGGCTGGGA AGGTAATTGA      1680

ATACTCGAGT TTAAAAGGAA AGCACATCCT TTTAAACCAA AACACACCTG CTGGGCTGTA      1740

AACAGCTTTT AGTGACATTA CCATCTACTC TGAAAATCTA ACAAAGGAGT GATTTGTGCA      1800

GTTGAAAGTA GGATTTGCTT CATAAAAGTC ACAATTTGAA TTCATTTTTG CTTTTAAATC      1860

CAGCCAACCT TTTCTGTCTT AAAAGGAAAA AAAAAA                                1896
```

(2) INFORMATION FOR SEQ ID NO:2:

(i) SEQUENCE CHARACTERISTICS:
        (A) LENGTH:  9 amino acid residues
        (B) TYPE:   amino acids
        (D) TOPOLOGY: linear (xi) SEQUENCE DESCRIPTION:  SEQ ID NO: 2:

Glu Glu Lys Leu Ile Val Val Leu Phe
5

(2) INFORMATION FOR SEQ ID NO: 3:

(i) SEQUENCE CHARACTERISTICS:
        (A) LENGTH: 9 amino acids
        (B) TYPE: amino acid
        (D) TOPOLOGY: linear (ii) MOLECULE TYPE: protein (ix) FEATURE:
        (A) NAME/KEY: HLA-B44 binding peptide (xi) SEQUENCE DESCRIPTION: SEQ ID NO: 3:

Ser Glu Ile Trp Arg Asp Ile Asp Phe
            5

(2) INFORMATION FOR SEQ ID NO: 4:

(i) SEQUENCE CHARACTERISTICS:
        (A) LENGTH:10 amino acids
        (B) TYPE: amino acid
        (D) TOPOLOGY: linear (ii) MOLECULE TYPE: protein (ix) FEATURE:
        (A) NAME/KEY:  Khanna peptide (xi) SEQUENCE DESCRIPTION: SEQ ID NO: 4:

Glu Glu Asn Leu Leu Asp Phe Val Arg Phe
           5               10

(2) INFORMATION FOR SEQ ID NO: 5:

(i) SEQUENCE CHARACTERISTICS:
        (A) LENGTH:    18 base pairs
        (B) TYPE:      nucleic acid
        (C) STRANDEDNESS: single
        (D) TOPOLOGY:  linear (ii) MOLECULE TYPE: nucleic acid (ix) FEATURE:
        (A) NAME/KEY:  PCR primer (xi) SEQUENCE DESCRIPTION: SEQ ID NO: 5:

GCCGGAGTAT TGGGACGA                                                            18

(2) INFORMATION FOR SEQ ID NO: 6:

(i) SEQUENCE CHARACTERISTICS:
        (A) LENGTH:     17 base pairs
        (B) TYPE:       nucleic acid
        (C) STRANDEDNESS: single
        (D) TOPOLOGY:   linear (ii) MOLECULE TYPE: nucleic acid (ix) FEATURE:
        (A) NAME/KEY:   PCR primer (xi) SEQUENCE DESCRIPTION: SEQ ID NO: 6:

GGCCGCCTCC CACTTGC                                                             17

(2) INFORMATION FOR SEQ ID NO: 7:

(i) SEQUENCE CHARACTERISTICS:
        (A) LENGTH:     19 base pairs
        (B) TYPE:       nucleic acid
        (C) STRANDEDNESS: single
        (D) TOPOLOGY:   linear (ii) MOLECULE TYPE: nucleic acid (ix) FEATURE:
        (A) NAME/KEY:   PCR primer (xi) SEQUENCE DESCRIPTION: SEQ ID NO: 7:

GGAGTATTGG GACCGGAAG                                                           19

(2) INFORMATION FOR SEQ ID NO: 8:

(i) SEQUENCE CHARACTERISTICS:
        (A) LENGTH:     17 base pairs
        (B) TYPE:       nucleic acid
        (C) STRANDEDNESS: single
        (D) TOPOLOGY:   linear (ii) MOLECULE TYPE: nucleic acid (ix) FEATURE:
        (A) NAME/KEY:   PCR primer (xi) SEQUENCE DESCRIPTION: SEQ ID NO: 8:

GGCCGCCTCC CACTTGT                                                             17

(2) INFORMATION FOR SEQ ID NO: 9:

(i) SEQUENCE CHARACTERISTICS:
        (A) LENGTH:     18 base pairs
        (B) TYPE:       nucleic acid
        (C) STRANDEDNESS: single
        (D) TOPOLOGY:   linear (ii) MOLECULE TYPE: nucleic acid (ix) FEATURE:
        (A) NAME/KEY:   PCR primer (xi) SEQUENCE DESCRIPTION: SEQ ID NO: 9:

CGCCACGAGT CCGAGGAT                                                            18

(2) INFORMATION FOR SEQ ID NO: 10:

```
       (i) SEQUENCE CHARACTERISTICS:
           (A) LENGTH:    18 base pairs
           (B) TYPE:      nucleic acid
           (C) STRANDEDNESS:  single
           (D) TOPOLOGY:  linear (ii) MOLECULE TYPE: nucleic acid (ix) FEATURE:
           (A) NAME/KEY:  PCR primer (xi) SEQUENCE DESCRIPTION: SEQ ID NO: 10:

CCTTGCCGTC GTAGGCTA                                                    18

(2) INFORMATION FOR SEQ ID NO: 11:

(i) SEQUENCE CHARACTERISTICS:
           (A) LENGTH:    18 base pairs
           (B) TYPE:      nucleic acid
           (C) STRANDEDNESS:  single
           (D) TOPOLOGY:  linear (ii) MOLECULE TYPE: nucleic acid (ix) FEATURE:
           (A) NAME/KEY:  PCR primer (xi) SEQUENCE DESCRIPTION: SEQ ID NO: 11:

CGCCACGAGT CCGAGGAA                                                    18

(2) INFORMATION FOR SEQ ID NO: 12:

(i) SEQUENCE CHARACTERISTICS:
           (A) LENGTH:    18 base pairs
           (B) TYPE:      nucleic acid
           (C) STRANDEDNESS:  single
           (D) TOPOLOGY:  linear (ii) MOLECULE TYPE: nucleic acid (ix) FEATURE:
           (A) NAME/KEY:  PCR primer (xi) SEQUENCE DESCRIPTION: SEQ ID NO: 12:

CCTTGCCGTC GTAGGCGT                                                    18

(2) INFORMATION FOR SEQ ID NO: 13:

(i) SEQUENCE CHARACTERISTICS:
           (A) LENGTH:    19 base pairs
           (B) TYPE:      nucleic acid
           (C) STRANDEDNESS:  single
           (D) TOPOLOGY:  linear (ii) MOLECULE TYPE: nucleic acid (ix) FEATURE:
           (A) NAME/KEY:  PCR primer (xi) SEQUENCE DESCRIPTION: SEQ ID NO: 13:

CCGAGTGAAC CTGCGGAAA                                                   19

(2) INFORMATION FOR SEQ ID NO: 14:

(i) SEQUENCE CHARACTERISTICS:
           (A) LENGTH:    19 base pairs
           (B) TYPE:      nucleic acid
           (C) STRANDEDNESS:  single
           (D) TOPOLOGY:  linear (ii) MOLECULE TYPE: nucleic acid
```

```
    (ix) FEATURE:
         (A) NAME/KEY:  PCR primer (xi) SEQUENCE DESCRIPTION: SEQ ID NO: 14:

GGTCGCAGCC ATACATCCA                                                      19

(2) INFORMATION FOR SEQ ID NO: 15:

(i) SEQUENCE CHARACTERISTICS:
         (A) LENGTH:    19 base pairs
         (B) TYPE:      nucleic acid
         (C) STRANDEDNESS:  single
         (D) TOPOLOGY:  linear (ii) MOLECULE TYPE: nucleic acid (ix) FEATURE:
         (A) NAME/KEY:  PCR primer (xi) SEQUENCE DESCRIPTION: SEQ ID NO: 15:

TACAAGCGCC AGGCACAGG                                                      19

(2) INFORMATION FOR SEQ ID NO:   16:

(i) SEQUENCE CHARACTERISTICS:
         (A) LENGTH:    18 base pairs
         (B) TYPE:      nucleic acid
         (C) STRANDEDNESS:  single
         (D) TOPOLOGY:  linear (ii) MOLECULE TYPE: nucleic acid (ix) FEATURE:
         (A) NAME/KEY:  PCR primer (xi) SEQUENCE DESCRIPTION: SEQ ID NO: 16:

CTCCAGGTAG GCTCTGTC                                                       18

(2) INFORMATION FOR SEQ ID NO:   17:

(i) SEQUENCE CHARACTERISTICS:
         (A) LENGTH:    10 amino acids
         (B) TYPE:      amino acid
         (D) TOPOLOGY:  linear (ii) MOLECULE TYPE:  protein (xi) SEQUENCE DESCRIPTION: SEQ ID NO: 17:

Met Glu Val Asp Pro Ile Gly His Leu Tyr
                 5                  10

(2) INFORMATION FOR SEQ ID NO:   18:

(i) SEQUENCE CHARACTERISTICS:
         (A) LENGTH:    9 amino acids
         (B) TYPE:      amino acid
         (D) TOPOLOGY:  linear (ii) MOLECULE TYPE:  protein (xi) SEQUENCE DESCRIPTION: SEQ ID NO: 18:

Glu Glu Lys Leu Ile Val Val Ala Phe
                 5

(2) INFORMATION FOR SEQ ID NO:   19:

(i) SEQUENCE CHARACTERISTICS:
         (A) LENGTH:    9 amino acids
```

```
            (B) TYPE:        amino acid
            (D) TOPOLOGY:    linear (ii) MOLECULE TYPE: protein (xi) SEQUENCE DESCRIPTION: SEQ ID NO: 19:

Phe Leu Arg Gly Arg Ala Tyr Gly Leu
                  5

(2) INFORMATION FOR SEQ ID NO: 20:

(i) SEQUENCE CHARACTERISTICS:
            (A) LENGTH:      9 amino acids
            (B) TYPE:        amino acid
            (D) TOPOLOGY:    linear (ii) MOLECULE TYPE: protein (ix) FEATURE:
            (D) OTHER INFORMATION: The first Xaa is preferably Glu or Met;
                  the second
                  Xaa is preferably Lys or Val; the third Xaa is
                  preferably Leu or Asp; the fourth Xaa is preferably
                  Ile or Pro; the fifth Xaa is preferably Val or Ile;
                  the sixth Xaa is preferably Val or Gly; the seventh
                  Xaa is preferably Leu, Ala or His.

(xi) SEQUENCE DESCRIPTION: SEQ ID NO: 20:

Xaa Glu Xaa Xaa Xaa Xaa Xaa Xaa Phe
                  5

(2) INFORMATION FOR SEQ ID NO: 21:

(i) SEQUENCE CHARACTERISTICS:
            (A) LENGTH:      9 amino acids
            (B) TYPE:        amino acid
            (D) TOPOLOGY:    linear (ii) MOLECULE TYPE: protein (ix) FEATURE:
            (D) OTHER INFORMATION:The first Xaa is preferably Glu or Met;
                  the second Xaa is preferably Lys or Val;
                  the third Xaa is preferably Leu or Asp; the
                  fourth Xaa is preferably Ile or Pro; the fifth
                  Xaa is preferably Val or Ile;
                  the sixth Xaa is preferably Val or Gly; the seventh
                  Xaa is preferably Leu, Ala or His.

(xi) SEQUENCE DESCRIPTION: SEQ ID NO: 21:

Xaa Glu Xaa Xaa Xaa Xaa Xaa Xaa Tyr
                  5

(2) INFORMATION FOR SEQ ID NO: 22:

(i) SEQUENCE CHARACTERISTICS:
            (A) LENGTH:      10 amino acids
            (B) TYPE:        amino acid
            (D) TOPOLOGY:    linear (ii) MOLECULE TYPE: protein (ix) FEATURE:
            (D) OTHER INFORMATION:The first Xaa is preferably Glu or Met;
                  the second
                  Xaa is preferably Lys or Val; the third Xaa is
                  preferably Leu or Asp; the fourth Xaa is preferably
                  Ile or Pro; the fifth Xaa is preferably Val or Ile;
                  the sixth Xaa is preferably Val or Gly; the seventh
                  Xaa is preferably Leu, Ala or His; the eighth Xaa
                  is preferably Leu (xi) SEQUENCE DESCRIPTION: SEQ ID NO: 22:
```

```
Xaa Glu Xaa Xaa Xaa Xaa Xaa Xaa Xaa Phe
            5
```

(2) INFORMATION FOR SEQ ID NO: 23:

(i) SEQUENCE CHARACTERISTICS:
        (A) LENGTH:    10 amino acids
        (B) TYPE:      amino acid
        (D) TOPOLOGY:  linear (ii) MOLECULE TYPE: protein (ix) FEATURE:
        (D) OTHER INFORMATION: The first Xaa is preferably Glu or Met;
            the second
            Xaa is preferably Lys or Val; the third Xaa is
            preferably Leu or Asp; the fourth Xaa is preferably
            Ile or Pro; the fifth Xaa is preferably Val or Ile;
            the sixth Xaa is preferably Val or Gly; the seventh
            Xaa is preferably Leu, Ala or His; the eighth Xaa
            is preferably Leu (xi) SEQUENCE DESCRIPTION: SEQ ID NO: 23:

```
Xaa Glu Xaa Xaa Xaa Xaa Xaa Xaa Xaa Tyr
            5
```

(2) INFORMATION FOR SEQ ID NO: 24:

(i) SEQUENCE CHARACTERISTICS:
        (A) LENGTH:    9 amino acids
        (B) TYPE:      amino acid
        (D) TOPOLOGY:  linear (ii) MOLECULE TYPE: protein (ix) FEATURE:
        (D) OTHER INFORMATION:    Each Xaa is any amino acid (xi) SEQUENCE DESCRIPTION: SEQ ID NO: 24:

```
Xaa Glu Xaa Xaa Xaa Val Xaa Xaa Phe
            5
```

(2) INFORMATION FOR SEQ ID NO: 25:

(i) SEQUENCE CHARACTERISTICS:
        (A) LENGTH:    10 amino acids
        (B) TYPE:      amino acid
        (D) TOPOLOGY:  linear (ii) MOLECULE TYPE: protein (ix) FEATURE:
        (D) OTHER INFORMATION:    Each Xaa is any amino acid (xi) SEQUENCE DESCRIPTION: SEQ ID NO: 25:

```
Xaa Glu Xaa Xaa Xaa Xaa Val Xaa Xaa Phe
            5                   10
```

(2) INFORMATION FOR SEQ ID NO: 26:

(i) SEQUENCE CHARACTERISTICS:
        (A) LENGTH:    9 amino acids
        (B) TYPE:      amino acid
        (D) TOPOLOGY:  linear (ii) MOLECULE TYPE: protein (ix) FEATURE:
        (D) OTHER INFORMATION: Each Xaa May be any amino acid except
            the carboxy
            terminal, which may be Tyr or Phe (xi) SEQUENCE DESCRIPTION: SEQ ID NO: 26:

Xaa Glu Xaa Xaa Ile Xaa Xaa Xaa Xaa
                5

(2) INFORMATION FOR SEQ ID NO: 27:

(i) SEQUENCE CHARACTERISTICS:
       (A) LENGTH:    10 amino acids
       (B) TYPE:      amino acid
       (D) TOPOLOGY:  linear (ii) MOLECULE TYPE:  protein (ix) FEATURE:
       (D) OTHER INFORMATION:  Each Xaa may be any amino acid except
           the carboxy
           terminal, which may be Tyr or Phe (xi) SEQUENCE DESCRIPTION: SEQ ID NO: 27:

Xaa Glu Xaa Xaa Xaa Ile Xaa Xaa Xaa Xaa
                5                  10

ISOLATED PEPTIDE DEFINED BY SEQ ID NO: 17 AND USES THEREOF

RELATED APPLICATION

This application is a divisional of Ser. No. 08/531,864, filed Sep. 21, 1995, now U.S. Pat. No. 5,977,300, which a continuation-in-part of Ser. No. 08/373,636, filed on Jan. 17, 1995, now U.S. Pat. No. 5,997,870 which is in turn a continuation-in-part of application Ser. No. 08/253,503 filed Jun. 3, 1994 now U.S. Pat. No. 5,589,334. Both applications are incorporated by reference.

FIELD OF THE INVENTION

This invention relates to isolated peptides, derived from tumor rejection antigen precursors and presented by HLA molecules, HLA-B44 in particular, and uses thereof. In addition, it relates to the ability to identify those individuals diagnosed with conditions characterized by cellular abnormalities whose abnormal cells present complexes of these peptides and HLA molecules, the presented peptides, and the ramifications thereof.

BACKGROUND AND PRIOR ART

The process by which the mammalian immune system recognizes and reacts to foreign or alien materials is a complex one. An important facet of the system is the T cell response. This response requires that T cells recognize and interact with complexes of cell surface molecules, referred to as human leukocyte antigens ("HLA"), or major histocompatibility complexes ("MHCs"), and peptides. The peptides are derived from larger molecules which are processed by the cells which also present the HLA/MHC molecule. See in this regard Male et al., *Advanced Immunology* (J.P. Lipincott Company, 1987), especially chapters 6–10. The interaction of T cell and complexes of HLA/peptide is restricted, requiring a T cell specific for a particular combination of an HLA molecule and a peptide. If a specific T cell is not present, there is no T cell response even if its partner complex is present. Similarly, there is no response if the specific complex is absent, but the T cell is present. This mechanism is involved in the immune system's response to foreign materials, in autoimmune pathologies, and in responses to cellular abnormalities. Recently, much work has focused on the mechanisms by which proteins are processed into the HLA binding peptides. See, in this regard, Barinaga, Science 257: 880 (1992); Fremont et al., Science 257: 919 (1992); Matsumura et al., Science 257: 927 (1992); Latron et al., Science 257: 964 (1992).

The mechanism by which T cells recognize cellular abnormalities has also been implicated in cancer. For example, in PCT application PCT/US92/04354, filed May 22, 1992, published on Nov. 26, 1992, and incorporated by reference, a family of genes is disclosed, which are processed into peptides which, in turn, are expressed on cell surfaces, which can lead to lysis of the tumor cells by specific CTLs. The genes are said to code for "tumor rejection antigen precursors" or "TRAP" molecules, and the peptides derived therefrom are referred to as "tumor rejection antigens" or "TRAs". See Traversari et al., Immunogenetics 35: 145 (1992); van der Bruggen et al., Science 254: 1643 (1991), for further information on this family of genes. Also see U.S. Pat. No. 5,342,774, incorporated by reference.

In U.S. Pat. No. 5,405,940, the disclosure of which is incorporated by reference, nonapeptides are taught which bind to the HLA-A1 molecule. The reference teaches that given the known specificity of particular peptides for particular HLA molecules, one should expect a particular peptide to bind one HLA molecule, but not others. This is important, because different individuals possess different HLA phenotypes. As a result, while identification of a particular peptide as being a partner for a specific HLA molecule has diagnostic and therapeutic ramifications, these are only relevant for individuals with that particular HLA phenotype. There is a need for further work in the area, because cellular abnormalities are not restricted to one particular HLA phenotype, and targeted therapy requires some knowledge of the phenotype of the abnormal cells at issue.

The enzyme tyrosinase catalyzes the reaction converting tyrosine to dehydroxyphenylalanine or "DOPA" and appears to be expressed selectively in melanocytes (Muller et al., EMBO J 7: 2715 (1988)). An early report of cDNA for the human enzyme is found in Kwon, U.S. Patent No. 4,898, 814. A later report by Bouchard et al., J. Exp. Med. 169: 2029 (1989) presents a slightly different sequence. A great deal of effort has gone into identifying inhibitors for this enzyme, as it has been implicated in pigmentation diseases. Some examples of this literature include Jinbow, WO9116302; Mishima et al., U.S. Pat. No. 5,077,059, and Nazzaropor, U.S. Pat. No. 4,818,768. The artisan will be familiar with other references which teach similar materials.

U.S. patent application 08/081,673, filed Jun. 23, 1993 now U.S. Pat. No. 5,487,974 and incorporated by reference, teaches that tyrosinase may be treated in a manner similar to a foreign antigen or a TRAP molecule—i.e., it was found that in certain cellular abnormalities, such as melanoma, tyrosinase is processed and a peptide derived therefrom forms a complex with HLA molecules on certain abnormal cells. These complexes were found to be recognized by cytolytic T cells ("CTLs"), which then lyse the presenting cells. The ramifications of this surprising and unexpected phenomenon were discussed. Additional peptides have now been found which also act as tumor rejection antigens presented by HLA-A2 molecules. These are described in Serial No. 08/203,054, filed Feb. 28, 1994 now U.S. Pat. No. 5,530,096 and incorporated by reference.

U.S. patent application Ser. No. 08/233,305 filed Apr. 26, 1994 now U.S. Pat. No. 5,519,117 and incorporated by reference, disclosed that tyrosinase is also processed to an antigen presented by HLA-B44 molecules. The finding was of importance, because not all individuals are HLA-A2+. The fact that tyrosinase is processed to an HLA-B44 presented peptide, however, does not provide for a universal approach to diagnosis and treatment of all HLA-B44+ tumors, because tyrosinase expression is not universal. Further, the fact that tyrosinase is expressed by normal cells as well as tumor cells may suggest some caution in the therapeutic area.

Khanna, et al., J. Exp. Med. 176: 169–179 (July 1992), disclose an HLA-B44 binding peptide, which is discussed further infra. The Khanna peptide is not related to the peptides claimed herein.

Kita, et al., Hepatology 18(5): 1039–1044 (1993), teach a 20 amino acid peptide alleged to bind to HLA-B44 and to provoke lysis.

Thorpe, et al., Immunogenetics 40: 303–305 (1994), discuss alignment of two peptides found to bind to HLA-B44, and suggest a binding motif generally. The Thorpe disclosure speaks of a negatively charged amino acid at position 2, and one at position 9 which may be hydrophobic, or positively charged.

Fleischhauer, et al., Tissue Antigens 44: 311–317 (1994) contains a survey of HLA-B44 binding peptides.

It has now been found that the MAGE-3 also expresses a tumor rejection antigen precursor is processed to at least one tumor rejection antigen presented by HLA-B44 molecules. It is of interest that this peptide differs from a peptide also derived from MAGE-3 and known to bind to HLA-A1, by a single, added amino acid at the N-terminus. This, inter alia, is the subject of the invention disclosure which follows.

BRIEF DESCRIPTION OF THE FIGURES

FIGS. 10A–10C depict the lytic activity of anti-E CTL clone LB33-CTL-269/1 on autologous melanoma cells, while FIG. 10B shows production of TNF by the same CTL clone, following stimulation by LB33-MEL.B-1 cells. The stimulator cells (10,000/microwell) had been incubated for 16 hours with 3000 CTLs. The concentration of TNF released by the CTLs had been measured using TNF sensitive WEHI-164c13 cells. Anti HLA-A24 monoclonal antibody C7709A2 was used to inhibit CTL stimulation, by adding a 1/100 dilution of ascites fluid obtained from mice inoculated with the hybridoma cells.

FIGS. 11A and 11B show the results of assays, wherein SEQ ID NOS: 17, 18, 19 and 3 were tested in competitive binding assays.

DETAILED DESCRIPTION OF PREFERRED EMBODIMENTS

EXAMPLE 1

Melanoma cell line LB33-MEL which has been available to researchers for many years, was used in the following experiments. A clone derived therefrom was also used. The clone is referred to hereafter as LB33-MELc1.

Samples containing mononuclear blood cells were taken from patient LB33. The melanoma cell line was contacted to the mononuclear blood cell containing samples. The mixtures were observed for lysis of the melanoma cell lines, this lysis indicating that cytolytic T cells ("CTLs") specific for a complex of peptide and HLA molecule presented by the melanoma cells were present in the sample.

The lysis assay employed was a chromium release assay following Herin et al., Int. J. Cancer 39:390–396 (1987), the disclosure of which is incorporated by reference. The assay, however, is described herein. The target melanoma cells were grown in vitro, and then resuspended at $10^7$ cells/ml in DMEM, supplemented with 10 mM HEPES and 30% FCS (i.e., from fetal calf serum) and incubated for 45 minutes at 37° C. with 200 $\mu$Ci/ml of Na($^{51}$Cr)O$_4$. Labelled cells were washed three times with DMEM, supplemented with 10 mM Hepes. These were then resuspended in DMEM supplemented with 10 mM Hepes and 10% FCS, after which 100 ul aliquots containing $10^3$ cells, were distributed into 96 well microplates. Samples of PBLs were added in 100 ul of the same medium, and assays were carried out in duplicate. Plates were centrifuged for 4 minutes at 100 g, and incubated for four hours at 37° C. in a 5.5% CO$_2$ atmosphere.

Plates were centrifuged again, and 100 ul aliquots of supernatant were collected and counted. Percentage of $^{51}$Cr release was calculated as follows:

$$\% \ ^{51}Cr \ \text{release} = \frac{(ER-SR)}{(MR-SR)} \times 100$$

where ER is observed, experimental $^{51}$Cr release, SR is spontaneous release measured by incubating $10^3$ labeled cells in 200 ul of medium alone, and MR is maximum release, obtained by adding 100 ul 0.3% Triton X-100 to target cells.

Those mononuclear blood samples which showed high CTL activity were expanded and cloned via limiting dilution, and were screened again, using the same methodology.

The same method was used to test target K562 cells. When EBV-B cells were used, the only change was the replacement of DMEM medium by Hank's medium, supplemented with 5% FCS.

Figure 1A:
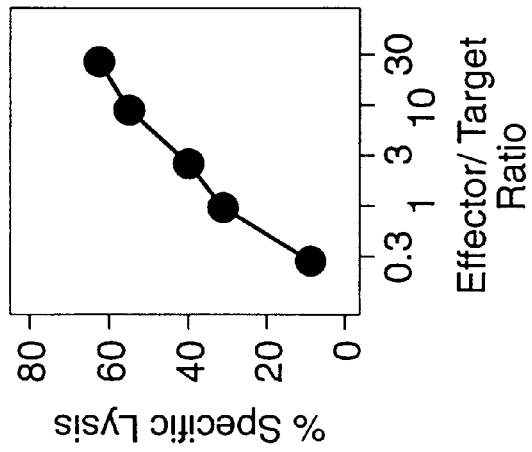
FIGS. 1A–1C shows the results of chromium release assays using each of three different cell lines (LB33-MELc1, LB33 EBV-B, and K562), and cytolytic T cell clone 159/5. The data are presented in terms of effector/target ratios vs % of lysis.
Figure 1B:
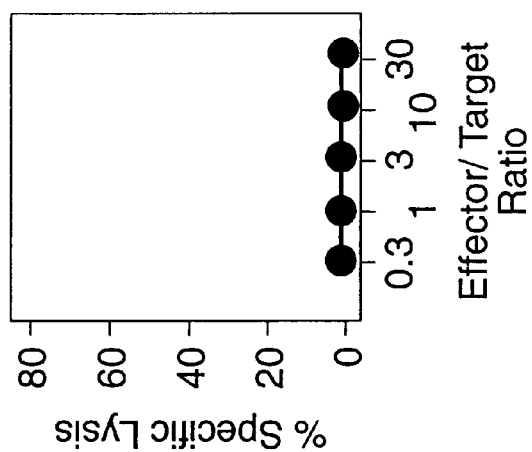
Figure 1C:
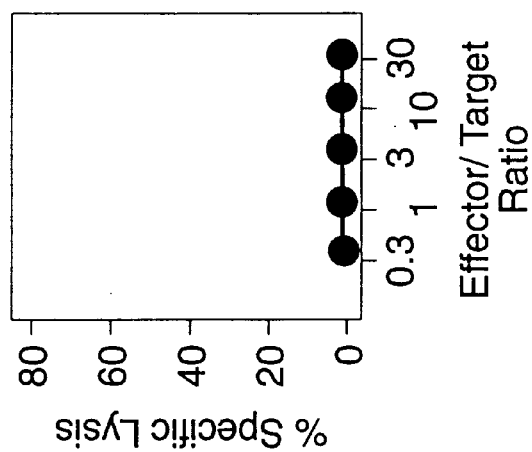

These experiments led to isolation of CTL clones LB33-CTL-159/5. FIG. 1 shows that this clone lysed tumor cells, but not EBV-B cells, or K562 cells.

Following the same protocol, a second CTL clone, i.e., LB33-CTL-159/3 was isolated. These lines will be referred to as "159/5" and "159/3", respectively. This second CTL has specificity differing from 159/5. This was ascertained following isolation of two antigen loss variants which (i) are lysed by 159/5 but not 159/3 and (ii) are not lysed by 159/5 and are lysed by 159/3. These variants are referred to as A⁻ and B⁻, respectively.

Figure 2:
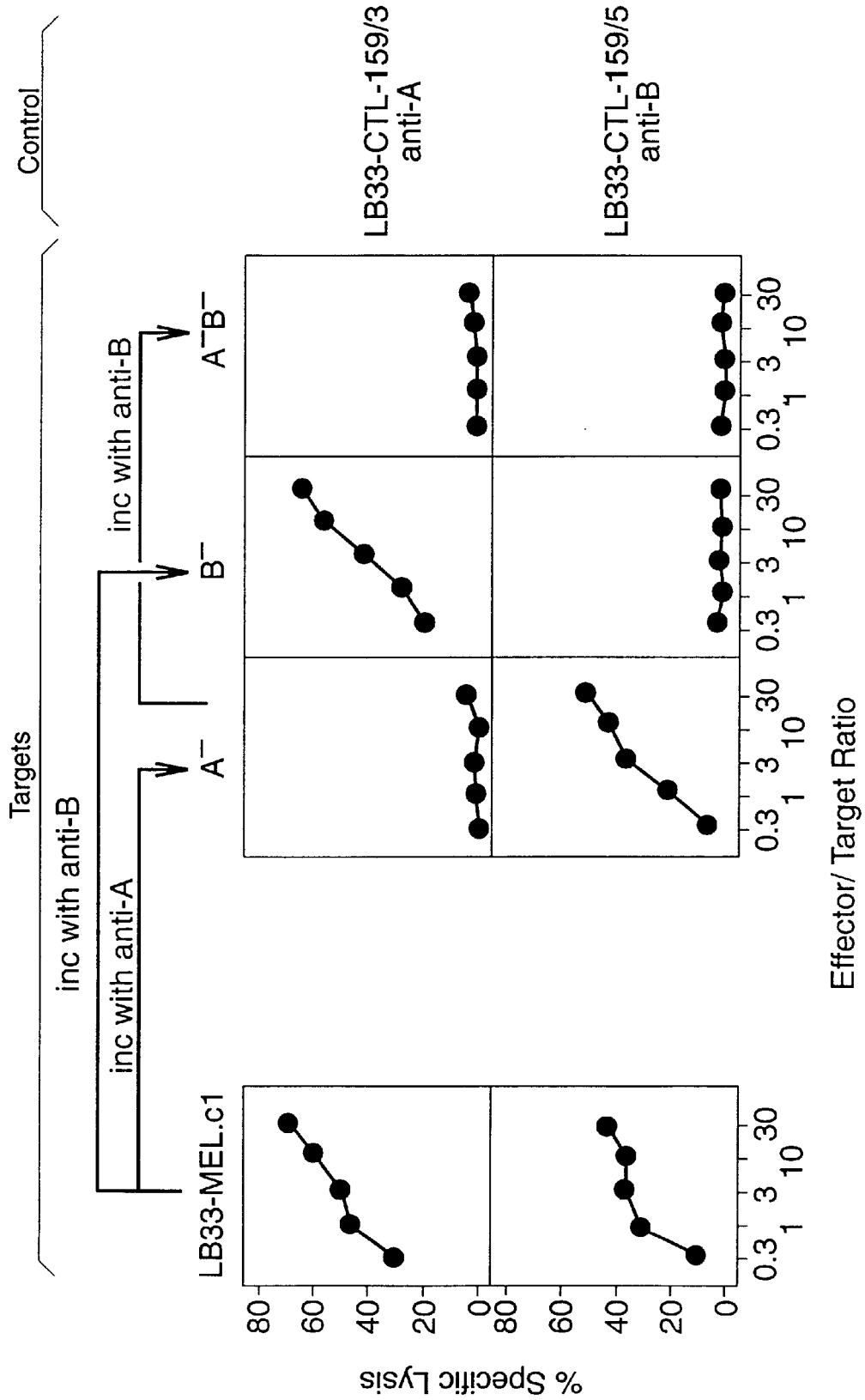
FIG. 2 shows the result of lysis studies which identified cell variants "A−" "B−", and "A−,B−". Again, a chromium release assay was used. Cell line LB33-MELc1 is $A^+B^+$, as is indicated by the positive lysis with both CTL lines tested. CTL 159/93 is anti-A, while CTL 159/5 is anti-B.

The A⁻ variant was then immunoselected with 159/5, and a third variant was obtained, which was not lysed by either 195/5 or 159/3. This variant is referred to as A⁻B⁻. FIG. 2 summarizes the results of the lysis assays, leading to isolation of the variants.

EXAMPLE 2

It was of interest to determine the pattern of HLA expression of variant A⁻B⁻. The patient from whom parent line LB33-MEL was derived was typed as HLA-A24, A28, B13, B44, Cw6, Cw7. When PCR expression analysis was carried out, it was found that both LB33-MELc1, and the B⁻ variant express all six alleles; however, the A-B⁻ variant does not express HLA-A28, B44, and Cw7. As a result, it was concluded that one of these HLA molecules presents the antigen leading to lysis by CTLs. The following example explores this further.

EXAMPLE 3

Figure 3:
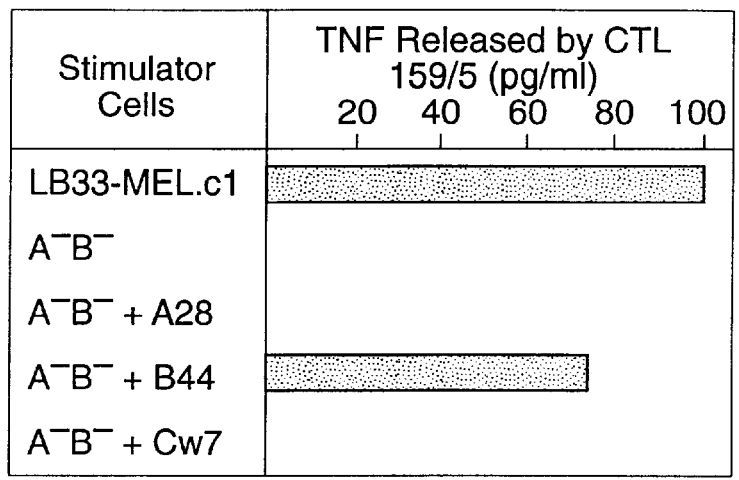
FIG. 3 shows results obtained when the variant $A^-B^-$ was transfected with coding sequences for each of HLA-A28, HLA-B 44, and HLA-Cw7, as compared to a control line. The results are depicted in terms of the sensitive TNF release assay (pg/ml), where CTL 159/5 was used.

Samples of the A⁻B⁻ variant were transfected by plasmid pcDNA-I/AmpI which had cloned therein, one of HLA-A28, HLA-B44, or HLA-Cw7. Following selection, the cells were tested in a TNF release assay, following Traversari, et al., Immunogenetics 35: 145–152 (1992), incorporated by reference herein. The results are summarized in FIG. 3, which shows that HLA-B44 is clearly implicated in the presentation of the antigen.

EXAMPLE 4

Once the presenting HLA molecule was identified, studies were carried out to identify the molecule, referred to hereafter as the "tumor rejection antigen precursor" or "TRAP" molecule which was the source of the presented peptide.

To do this, total mRNA was isolated from cell line LB33-MELc1. The messenger RNA was isolated using an oligo-dT binding kit, following well recognized techniques. Once the messenger RNA was secured, it was transcribed into cDNA, again using standard methodologies. The cDNA was then ligated to EcoRI adaptors and cloned into the EcoRI site of plasmid pcDNA-I/Amp, in accordance with manufacturer's instructions. The recombinant plasmids were then electrophorated into DH5α $E.\ coli$ (electroporation conditions: 1 pulse at 25 $\mu$farads, 2500 V).

The transfected bacteria were selected with ampicillin (50 $\mu$g/ml), and then divided into pools of 100 bacteria each. Each pool represented about 50 different cDNAs, as analysis showed that about 50% of plasmids contained an insert. Each pool was amplified to saturation, and plasmid DNA was isolated via alkaline lysis, potassium acetate precipitation and phenol extraction, following Maniatis et al., in Molecular Cloning: A Laboratory Manual (Cold Spring Harbor, N.Y., 1982). Cesium gradient centrifugation was not used.

The amplified plasmids were then transfected into eukaryotic cells. Samples of COS-7 cells were seeded, at 15,000 cells/well into tissue culture flat bottom microwells, in Dulbecco's modified Eagles Medium ("DMEM") supplemented with 10% fetal calf serum. The cells were incubated overnight at 37° C., medium was removed and then replaced by 30 $\mu$l/well of DMEM medium containing 10% Nu serum, 400 $\mu$g/ml DEAE-dextran, 100 $\mu$M chloroquine, and 100 ng of a plasmid containing cDNA for HLA-B44 from LB33. Following four hours of incubation at 37° C., the medium was removed, and replaced by 50 $\mu$l of PBS containing 10% DMSO. This medium was removed after two minutes and replaced by 200 $\mu$l of DMEM supplemented with 10% of FCS.

Following this change in medium, COS cells were incubated for 48 hours at 37° C. Medium was then discarded, and 2000 cells of 159/5 were added, in 100 $\mu$l of Iscove's medium containing 10% pooled human serum and 25 U/ml IL-2. Supernatant was removed after 24 hours, and TNF content was determined in an assay on WEHI cells, as described by Traversari et al., Immunogenetics 35: 145–152 (1992), the disclosure of which is incorporated by reference. One pool stimulated TNF release above background, and these bacteria were cloned, and used in the following experiment.

EXAMPLE 5

Plasmid DNA was extracted from the bacteria cloned in Example 4, transfected into a new sample of COS cells in the same manner as described supra, and the cells were again tested for stimulation of 159/5. A positive clone was found in clone 350/2, as demonstrated by data summarized in FIG. 4.

Figure 4A:
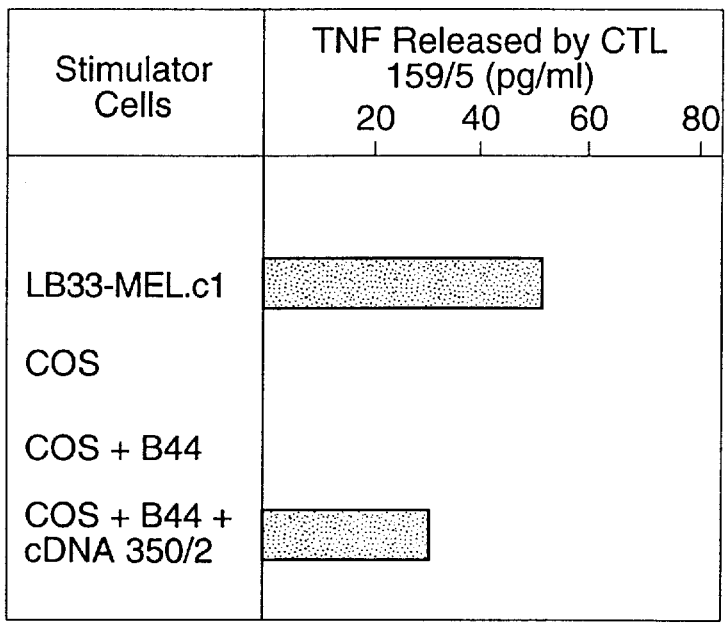
FIGS. 4A–4B show TNF release by CTL 159/5, where COS cells were transfected with HLA-B44, or HLA-B44 plus a nucleic acid molecule in accordance with this invention.
Figure 4B:
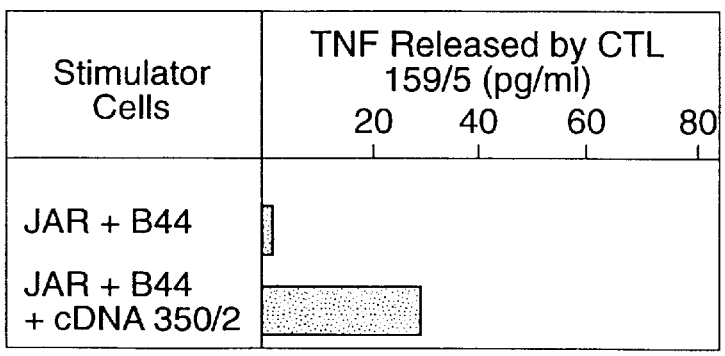
Figure 5A:
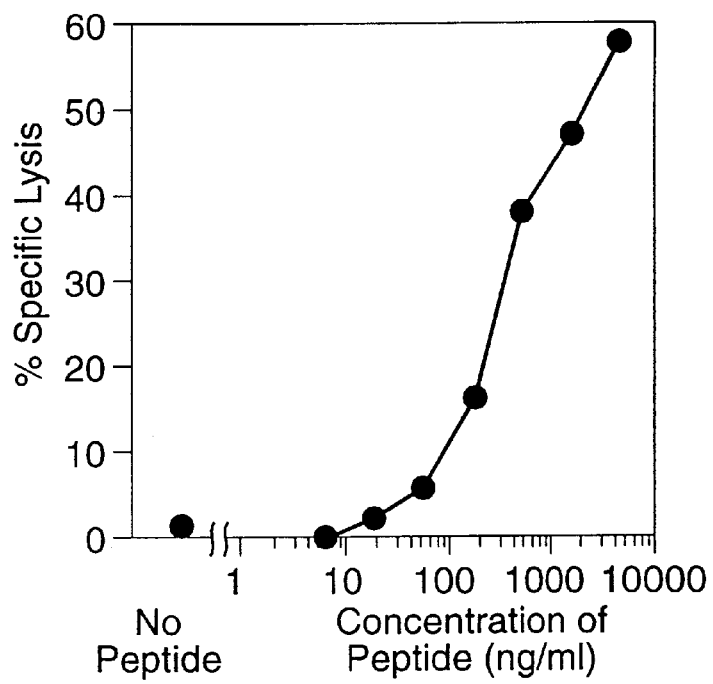
FIG. 5A depicts $^{51}$Cr release in EBV-B cells, when contacted with CTL 159/5.
Figure 5B:
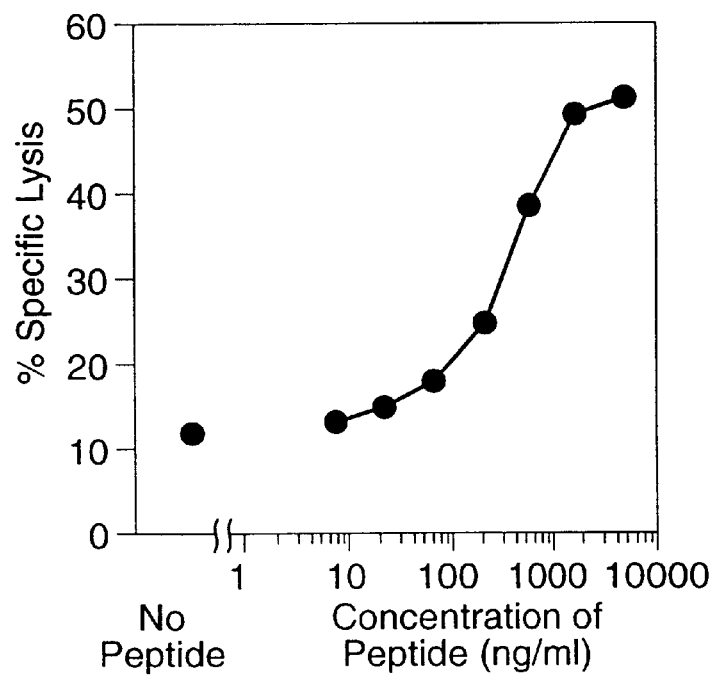
FIG. 5B is similar, but uses LB33-MEL B− cells. In each of FIGS. 5A and 5B, the antigenic peptide of the invention was contacted to the cells prior to contact with the CTLs.

In order to confirm the results obtained to this point, the human choriocarcinoma cell line JAR, which is readily available from the American Type Culture Collection, was used. This cell line does not express HLA molecules, nor is it recognized by CTL 159/5. When JAR was transfected with HLA-B44 cDNA, it was still not recognized by CTL 159/5. Co-transfection with HLA-B44 and 350/2 cDNAs, however, led to lysis, as is seen in FIG. 4.

The plasmid from the positive clone was removed, and sequenced following art known techniques. Information shows that the plasmid insert was 1896 base pairs long, and showed no homology with any sequences in data banks. The nucleotide sequence is set forth herein as SEQ ID NO: 1.

EXAMPLE 6

Figure 6:
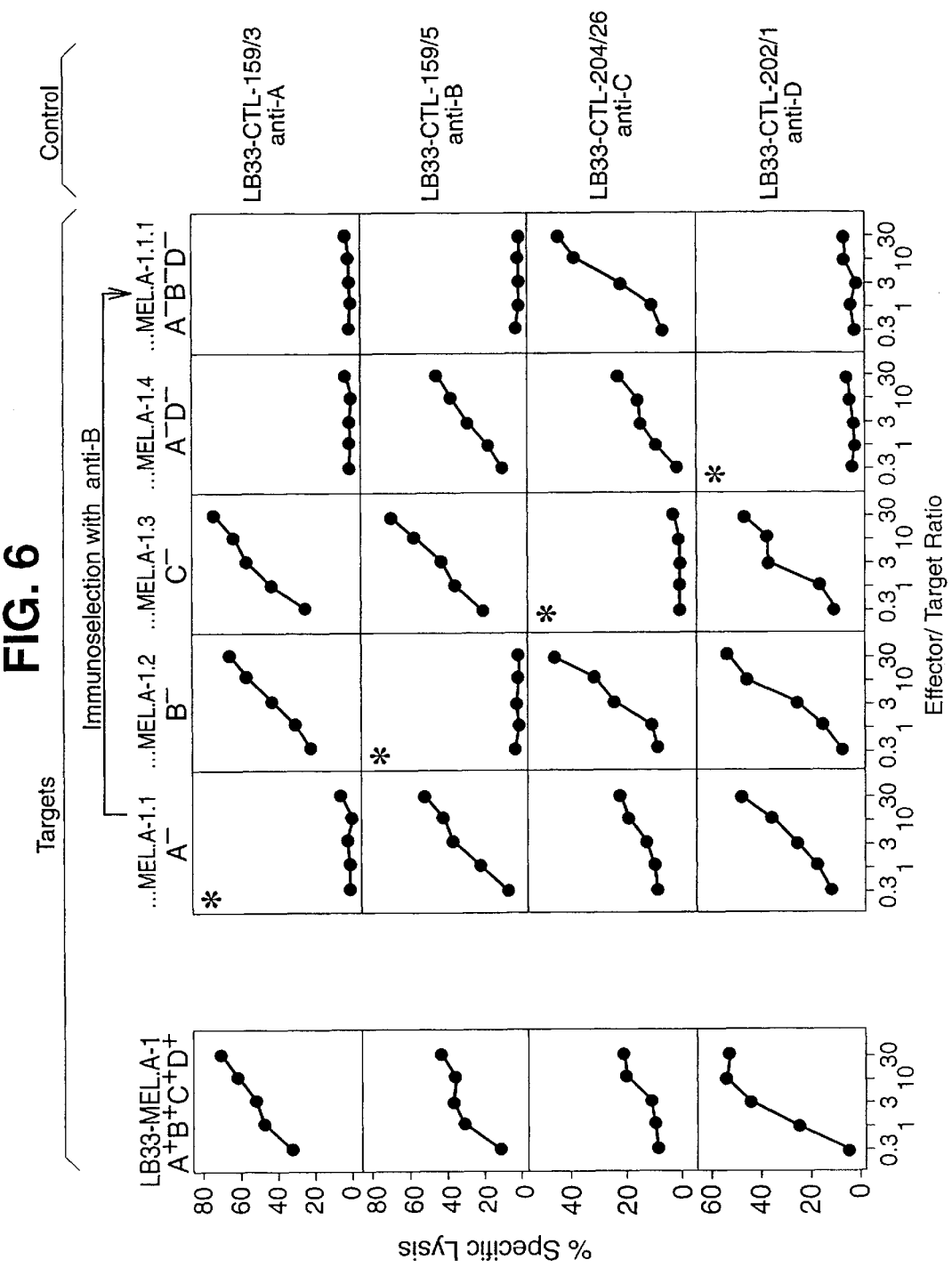
FIG. 6 shows the lytic activity of various autologous CTL clones on antigen loss variants derived from melanoma clonal line LB33.MEL.A-1.

In order to ascertain the peptide which was the tumor rejection antigen, fragments of SEQ ID NO: 1, averaging about 300 base pairs, were amplified via PCR, cloned into PcDNAI 1/Amp, and then cotransfected into COS cells with plasmid encoding HLA-B44, following the protocols of the preceding examples. These experiments led to identifying the region corresponding to amino acid residues 683–955 of SEQ ID NO: 1 as encoding the antigenic peptide. This region was compared to the peptide described by Khanna, et al., J. Exp. Med. 176: 169–176 (7/92), and the peptide described in Ser. No. 08/233,305, filed Apr. 26, 1994, now U.S. Pat. No. 5,519,117 i.e.:

Glu Glu Lys Leu Ile Val Val Leu Phe corresponds to these residues. As such, a peptide corresponding to this sequence was synthesized, and used to sensitize HLA-B44⁺ cell lines. The results are shown in FIGS. 6A and 6B, which depict the results of a $^{51}$Cr release assay using EBV transformed B cells (FIG. 6A), and the B⁻ variant described supra (FIG. 6B). The cells were incubated with varying concentrations of the peptide for 30 minutes at 37° C., before adding CTL 159/5 (effector/target ratio: 10:1). Half maximal lysis was obtained with 100-200 ng/ml of peptide.

EXAMPLE 7

Examples 1–6, set forth supra, describe work using the cell line LB33-Melc1. Additional cell lines were also derived from a cutaneous metastasis from patient LB33. One such line is LB33-MEL.A-1, which is used in the example which follows.

First, the cell line was used, in the same manner that the cell line of examples 1–6 was used (Herin et al., supra). Blood mononuclear cells ($10^6$/well), were stimulated with irradiated tumor cells ($3/10^5$ cells/well), in 2 ml of Iscove's medium, supplemented with 10% pooled human serum, asparagine-glutamine-arginine (36 mg/ml, 216 mg/ml, 116 mg/ml, respectively), 2-mercaptoethanol (0.05 mM), and 5 U/ml of human IL-4. IL-2 (10 U/ml) was added on the third day of cultivation. Sensitivity of the tumor cells to autologous CTLs was determined as in example 1, supra. The experiment yielded 82 stable cytolytic T lymphocytes, derived from seven independent cultures. All of these CTLs were $CD8^+$. They were specific for tumor cells in that they lysed LB33-MEL.A-1 cells, but not K562, or autologous, EBV transformed cells.

EXAMPLE 8

The fact that LB33-MEL.A-1 cells were lysed by autologous CTLs suggested the next experiment, which was to identify the antigens recognized by establishing antigen loss variants.

To do this, samples of the cell line were selected, four times, with the autologous CTL clone LB33-CTL 159/3, described supra. Each round of selection involved incubating, for 2–6 hours, $2-3 \times 10^7$ adherent tumor cells with a similar number of CTLs, in the same manner described supra. In each round, CTLs were washed away following the incubation, and the surviving adherent tumor cells were amplified prior to the next round of selection.

This procedure resulted in a clone resistant to CTL 159/3; however, when tested with additional autologous CTLs, it was found that CTL 159/5, described supra, did lyse the loss variant, as did additional CTL clones, including 204/26, and 202/1. Please see FIG. 6, the column labelled "MEL.A- 1.1". Similarly, additional cell lines were established which were not lysed by one of these four CTL clones, but was lysed by the others. Note FIG. 6. Thus, at least four different antigens were found to be presented on the surface of LB33-MEL.A-1, because four distinct antigen-loss variants were identified. As set forth in FIG. 6, then, LB33-MEL.A-1 is considered "$A^+B^+C^+D^+$" for antigen expression (lysed by all of CTL 159/3, 159/5, 204/26, and 202/1); MEL.A-1.1 is $A^-B^+C^+D^+$ (not lysed by 159/3, lysed by others); MEL.A-1.2 is $A^+B^-C^+D^+$ (not lysed by 159/5; lysed by others), MEL.A-1.3 is $A^+B^+C^-D^+$ (not lysed by 204/26; lysed by others), and MEL.A-1.4 is $A^-B^+C^+D^-$ (not lysed by 202/1 or 159/3). Further, cell line MEL.A-1.1.1 was isolated, which was $A^-B^-C^+D^-$ (lysed only by 204/26).

When the 82 CTLs identified via example 7 were tested on these lines, 29 anti-A, 29 anti-B, 10 anti-C, and 14 anti-D clones were identified, suggesting that there were no other antigens being presented.

Selection with anti-D CTL clone 202/1 led to identification of a line which was also resistant to the anti-A CTL clone (159/3), as did selection with anti-B CTL (i.e., the resulting $A^-B^-C^+D^-$ line). This result suggests that $A^-D^-$ and $A^-B^-D^-$ antigen loss variants were actually HLA loss variants, with antigens A, B and D sharing the same HLA presenting molecule, or that different class I molecules had been lost together with the antigen loss variants. The following experiments pursued this issue.

EXAMPLE 9

The patient from whom the LB33 cell lines had been developed had been serologically typed, previously, as HLA-A24, A28, B13, B44, Cw6, Cw7. Studies were then carried out to determine the expression of HLA class I genes by the cell lines.

Semi-quantitative conditions for DNA amplification by PCR were established in order to assess the expression of each of the six class I alleles by the different LB33-MEL tumor cell clones. The Amplification Refractory Mutation System (ARMS) PCR methodology proposed by Browning et al, that relies on the perfect nucleotide matched needed at the 3' end of primers to ensure specificity of DNA amplifications was used. See Browning et al, Proc. Natl. Acad. Sci. USA 90: 2842 (1993) incorporated by reference herein. On the basis of sequences obtained in typing LB33, allele-specific primers that enabled discrimination of each one of the six alleles from the five others (5' primer followed by 3' primer) were synthesized.

for A24: 5'-GCCGGAGTATTGGGACGA and 5'-GGCCGCCTCCCACTTGC (SEQ ID NOS: 5 and 6)

for A28: 5'-GGAGTATTGGGACCGGAAG and 5'-GGCCGCCTCCCACTTGT (SEQ ID NOS: 7 and 8)

for B13: 5'-CGCCACGAGTCCGAGGAT and 5'-CCTTGCCGTCGTAGGCTA (SEQ ID NOS: 9 and 10)

for B44: 5'-CGCCACGAGTCCGAGGAA and 5'-CCTTGCCGTCGTAGGCGT (SEQ ID NOS: 11 and 12)

for Cw6: 5'-CCGAGTGAACCTGCGGAAA and 5'-GGTCGCAGCCATACATCCA (SEQ ID NOS: 13 and 14)

for Cw7: 5'-TACAAGCGCCAGGCACAGG and 5'-CTCCAGGTAGGCTCTGTC (SEQ ID NOS: 15 and 16)

To carry out semi-quantitative measurements of expression, 27 cycles of PCR amplification of reverse transcribed RNA were carried out with each set of primers and DNA amplification was found to be in the linear range observed. The quantity of the amplified DNA was visually assessed with agarose gels stained with ethidium bromide. These quantities were compared to those obtained with a standard curve containing the products of RT-PCR amplification of serial dilutions of RNA from LB33-MEL.A-1 cells. The expression of samples was normalized for RNA integrity by taking into account the expression level of the β-actin gene. The results were expressed relative to the level of expression by LB33-MEL.A-1 cells. The results of this work are set forth in Table 1, which follows. A "+++" indicates expression corresponding to more than half that of the LB33-MEL.A-1 cells, "++" means that expression was between ⅛ and ½ of that of LB33-MEL.A-1, a "+" means that expression was less than ⅛ of that of LB33-MEL.A-1 expressed and "−" means there was no expression.

TABLE 1

Expression of HLA class I by the antigen-loss
variants derived from LB33-MEL.A-1 cells.

| LB33-MEL.A-1 | | LB33-MEL.A tumor cells | | | | |
|---|---|---|---|---|---|---|
| | | Antigen-loss variants | | | | |
| Expression of | | $A^-$ | $B^-$ | $C^-$ | $A^-D^-$ | $A^-B^-D^-$ |
| A. | | Gene Expression | | | | |
| A24 | +++ | +++ | +++ | − | ++ | +++ |
| A28 | +++ | +++ | +++ | +++ | + | − |
| B13 | +++ | +++ | +++ | + | +++ | +++ |
| B44 | +++ | +++ | +++ | +++ | ++ | − |
| Cw6 | +++ | +++ | +++ | + | +++ | +++ |
| Cw7 | +++ | ++ | +++ | +++ | + | − |

As seen, both MEL.A-1 cells, and $B^-$ variant expressed similar levels of all six HLA alleles. The A variant showed an approximately 4-fold decrease in expression of Cw7. The remaining antigen loss variants showed decreases in expression of sets of three alleles. For $C^-$ cells, reduced levels of expression for HLA-A24, B13, and Cw6 were found, while $A^-D^-$, and $A^-B^-D^-$ variants showed reduction in A28, B44, and Cw7 expression. This suggests that A24-B13-Cw6, and A28-B44-Cw7 constitute two HLA class I haplotypes of patient LB33, and that reduced expression of these haplotype probably accounted for loss of antigen expression by the immunoselected tumor cells.

EXAMPLE 10

The next experiments were designed to confirm a correlation between HLA gene expression, and lysis by CTLs. To do this, the expression of a given HLA gene, as determined supra, was compared with the results obtained using a standard antibody assay. Only A24, A28 and B13 were tested, using murine antibodies specific thereto (C7709A1 for A24; 2.28M1 for A28, and TÜ48 for B13). Binding of antibody was determined by incubation with antibody, washing and then contacting with goat anti-mouse Ig antibodies, coupled to fluorescein. The cells were then analyzed by flow cytometry, a standard technique.

Figure 7:
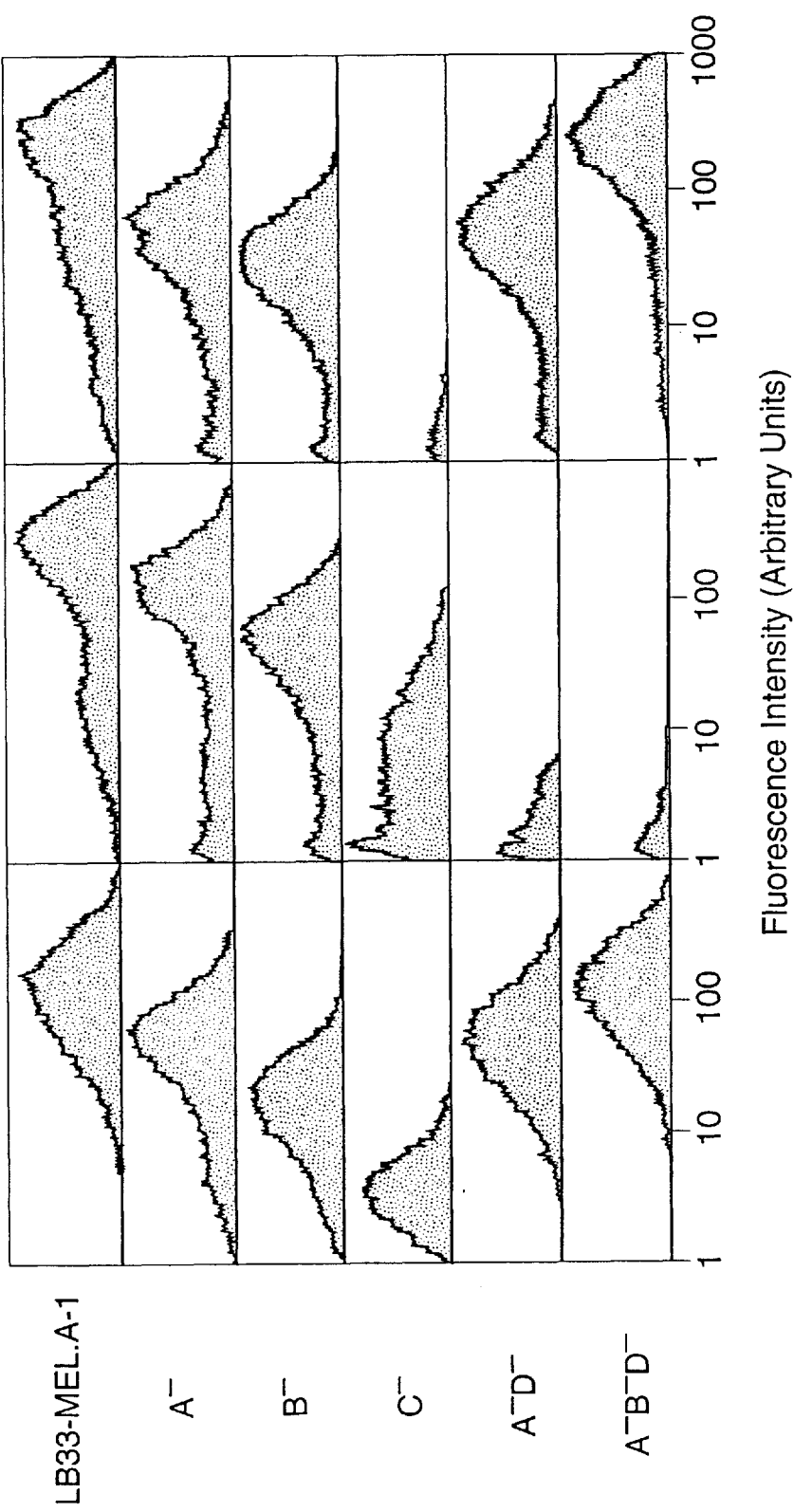
FIG. 7 presents results showing expression of HLA-A24, A28 and B13 molecules by antigen loss variants of LB33-MEL.A-1. Tumor cells had been incubated with mouse antibodies against particular HLA molecules, and were then labeled with fluorescein tagged goat anti-mouse antibodies.
Figure 8A:
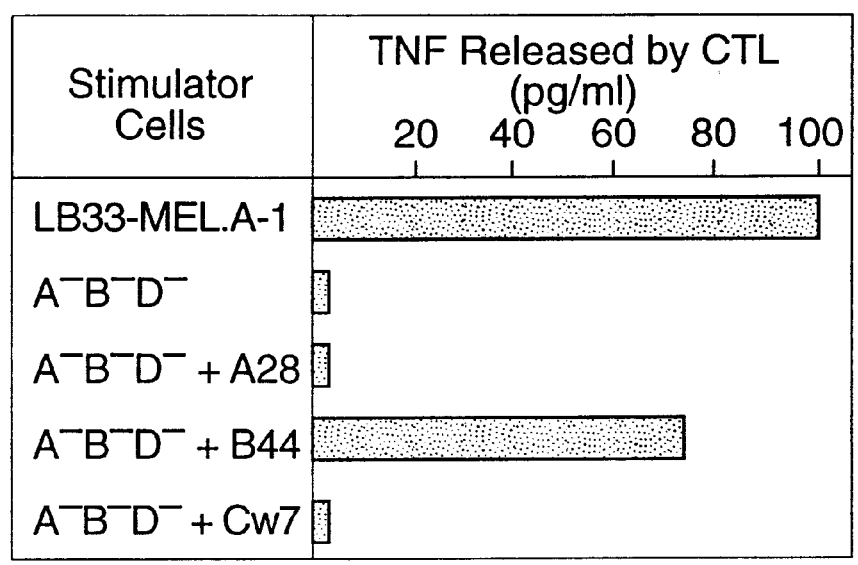
FIGS. 8A–8F show the production of tumor necrosis factor (TNF) by CTL clones stimulated by antigen loss variants, transfected with various HLA alleles. Untransfected LB33-MEL.A-1 cells were used as controls, as were antigen loss variants. The CTL clones used were 159/3, 159/5 and 204/26, corresponding to anti-A, anti-B, and anti-C CTLs, respectively.
Figure 8B:
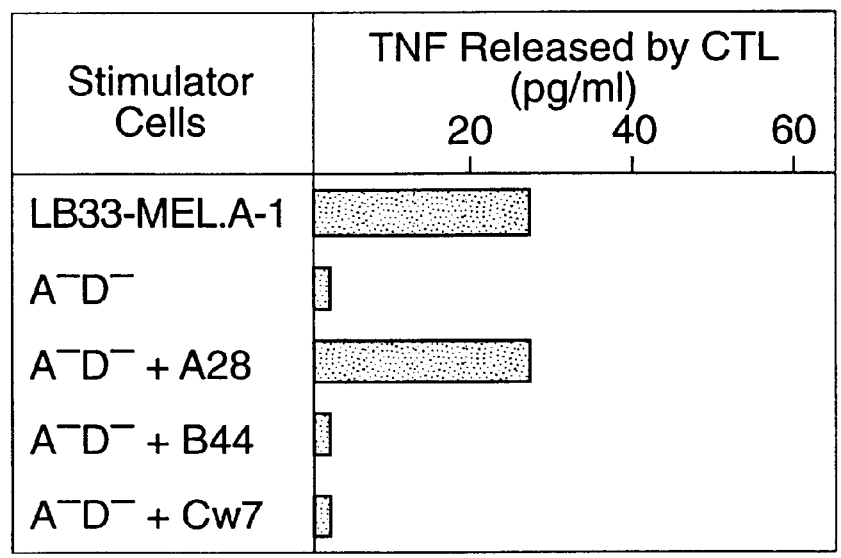
Figure 8C:
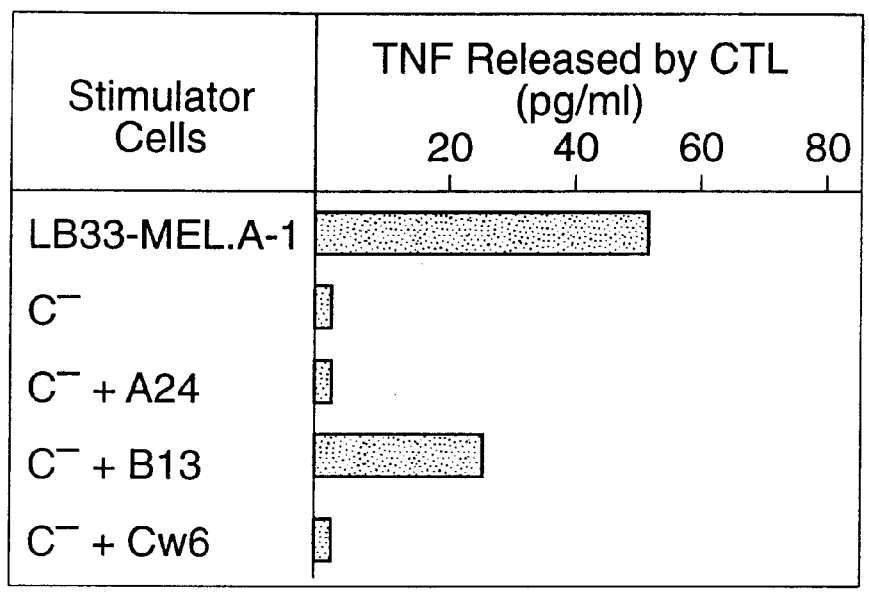
Figure 8D:
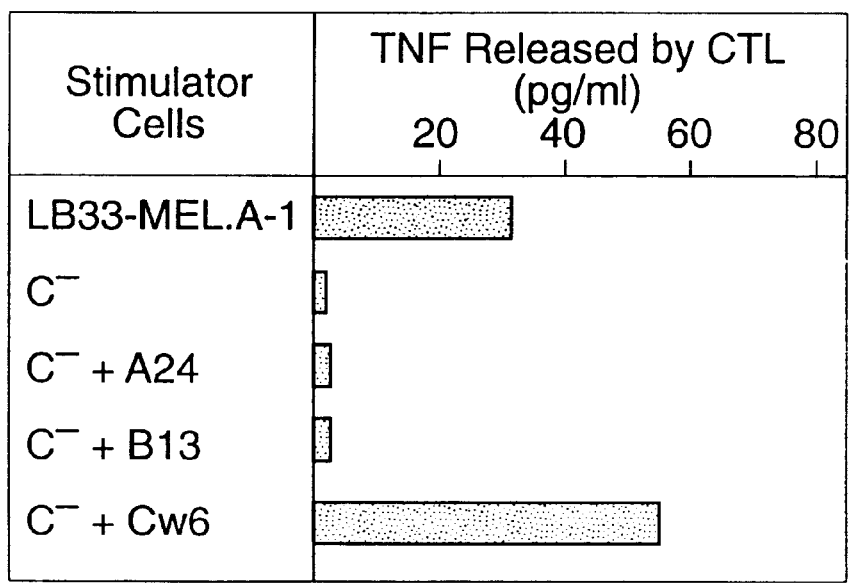
Figure 8E:
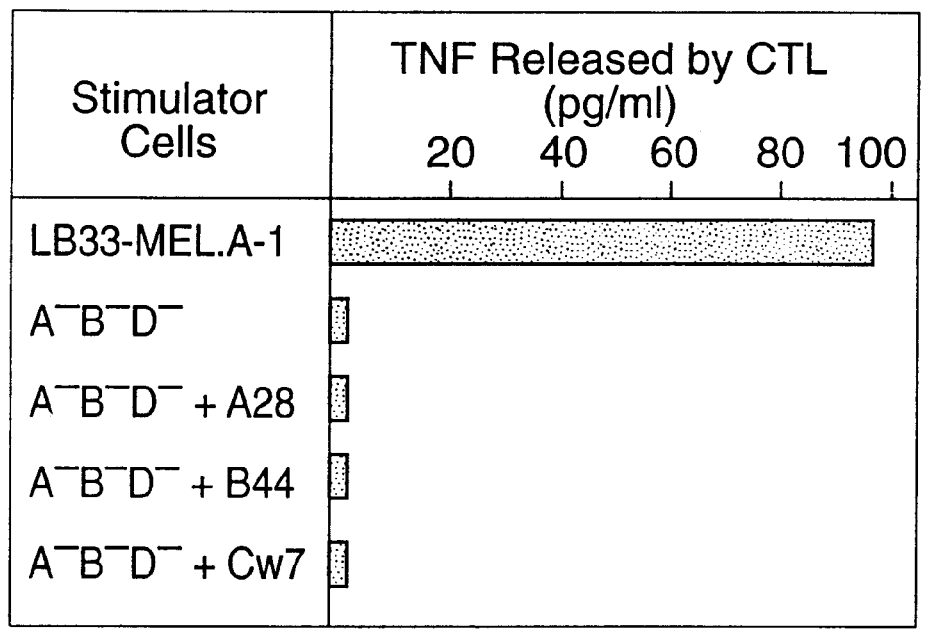
Figure 8F:
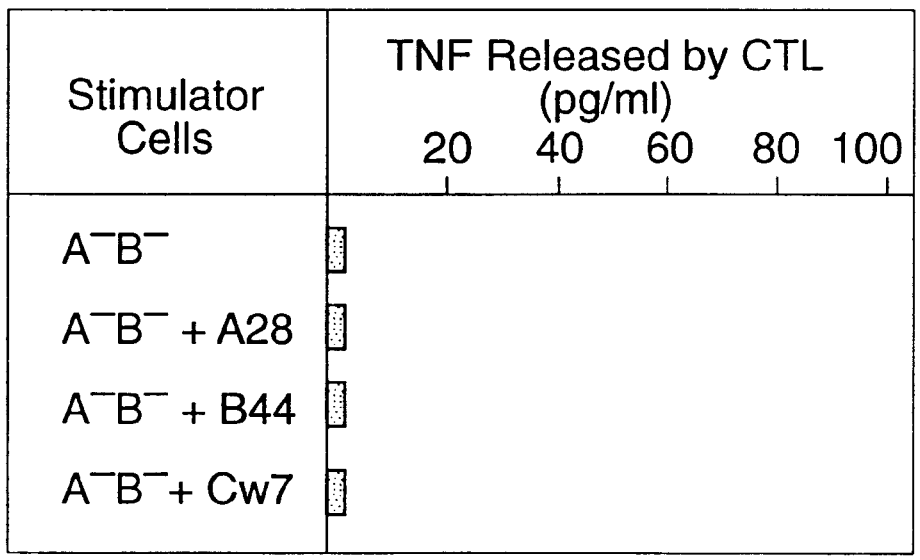

Table 2 summarizes the results, which are also shown in FIG. 7. In table 2 that follows, the indicated level of HLA expression corresponds to the mean intensity of fluorescence shown in FIG. 6. Values are expressed relative to levels found in LB33-MEL.A-1 cells.

It appears from these results that when levels of HLA expression estimated to range below ⅛ of that of LB33-MEL.A-1 cells, undetectable or barely detectable levels of HLA surface molecules are found, thus suggesting that antigen presentation to CTL was unlikely for the given HLA molecule.

In view of this, and assuming that $C^-$, $A^-D^-$ and $A^-B^-D^-$ selected cells had lost expression of antigen because of lack of HLA molecules, it appeared to be the case that the class I presenting molecules for antigen A were A28 or Cw7, B44 for antigen B, A24 or B13 or Cw6 for antigen C, and A28 or Cw7 for antigen D.

TABLE 2

| LB33-MEL.A-1 | Antigen-loss variants | | | | |
|---|---|---|---|---|---|
| Expression of | $A^-$ | $B^-$ | $C^-$ | $A^-D^-$ | $A^-B^-D^-$ |
| | Expression of surface antigen | | | | |
| A24 | 100 | 33 | 13 | 4 | 41 | 95 |
| A28 | 100 | 29 | 14 | 3 | 1 | 1 |
| B13 | 100 | 27 | 22 | 1 | 40 | 230 |

EXAMPLE 11

The experiments detailed above were followed by additional work to determine, definitively, the presenting molecules for the antigens expressed by the LB33-MEL.A cells. To do this, tumor cells which had lost expression of particular HLA class I molecules were transfected, using the classic calcium phosphate precipitation method, with expression vector pcDNA3, into which the particular class I cDNA was cloned. This vector contains the $neo^R$ marker. Transfectants were selected with 1.5 mg/ml of G418, and were then used to stimulate CTL clones, using the TNF assay set forth in the previous examples.

FIG. 8 depicts these results. Expression of antigen B was restored in $A^-B^-D^-$ cells by transfection with a plasmid carrying HLA-B44, but not with plasmids containing HLA-A28 or HLA-Cw7. The expression of antigen C was restored in $C^-$ cells by transfection with HLA B13. Four other anti-C CTL clones also recognized $C^-$ cells, but five other anti-C CTL clones, including depicted CTL 179C/50, did not; rather, these CTLs recognized $C^-$ cells transfected with HLA-Cw6. Thus, it may be concluded that there are two groups of anti-C CTL clones. One recognizes an antigen presented by HLA-B13, and the other an antigen presented by HLA-Cw6. As for antigen D, $A^-D^-$ cells were restored to $A^-D^+$ via transfection with HLA-A28. None of the cDNA restored expression of antigen A (i.e., tested HLA A28, B44, Cw7), although it clearly is presented by HLA-class I molecules, because lysis by anti-A CTLs is completely inhibited by anti-class I monoclonal antibody W6/32. It is possible that this antigen may be presented by a non-A, B, C class I molecule, of which two alleles were present in patient LB33, one of these being lost, together with the A28-B44-Cw7 haplotype in $A^-D^-$, $A^-B^-D^-$ cells.

The results for antigen C have led to a change in nomenclature. There are two antigens referred to as Antigen, Ca1 and antigen Cb, hereafter.

EXAMPLE 12

In further experiments, the question of whether or not cells of the line LB33-MEL.B could be recognized by autologous cell lines, was addressed.

Irradiated LB33-MEL.B.1 cells were used in the same manner as was used, supra (Herin, et al), to stimulate autologous lymphocytes. The lymphocytes had been taken from patient LB33 in 1990 or 1994.

Figure 9:
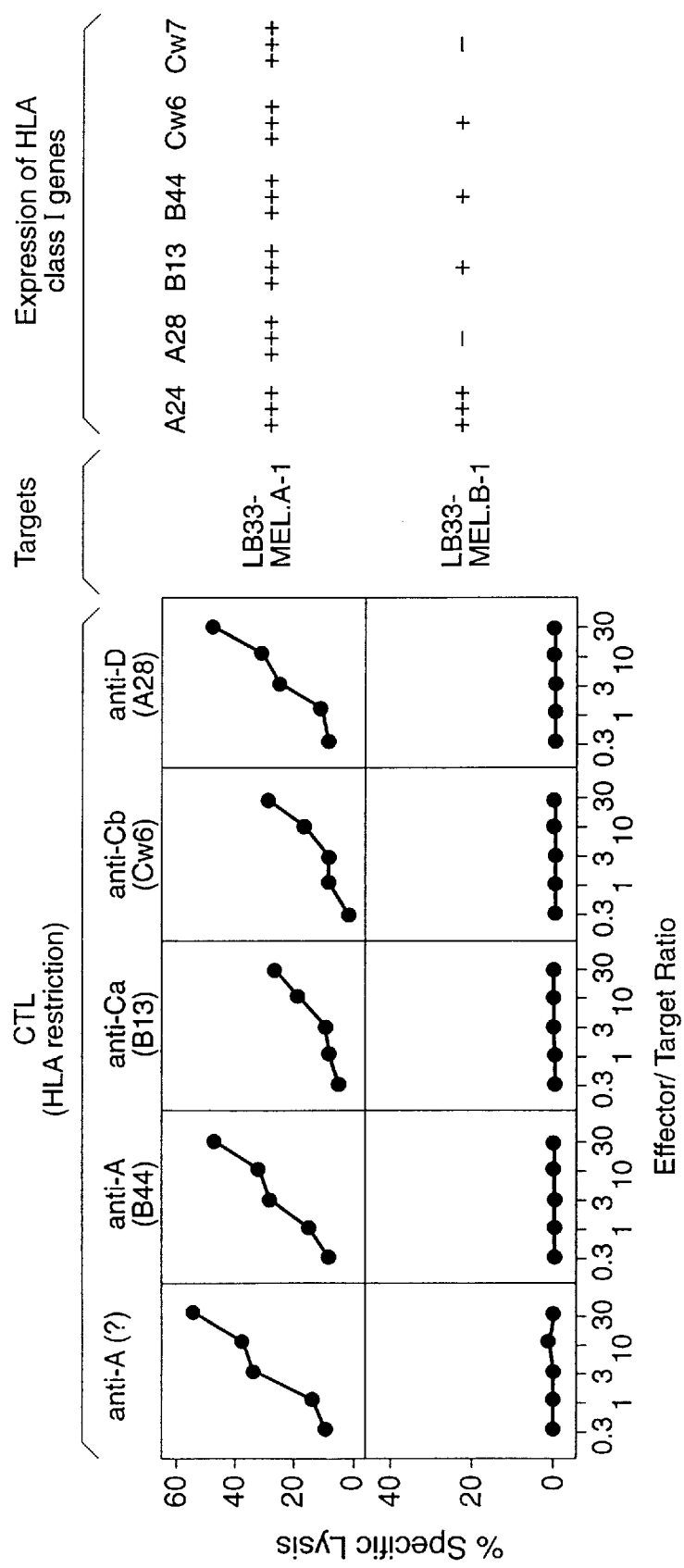
FIG. 9 sets forth data regarding cytolytic activity of lymphocytes obtained in autologous mixed lymphocyte-tumor cell cultures. The blood mononuclear cells had been isolated from patient LB33 in either March 1990 or January 1994. The cell line LB33-MEL.A had been obtained following surgery in 1988. Cell line LB33-MEL.B was obtained from a metastasis which developed in the patient in 1993.

As is shown in FIG. 9, only the lymphocytes from 1994 lysed LB33-MEL.B-1 cells; however, they did not lyse LB33-MEL.A cells. Thus, the LB33-MEL.B-1 line presents an antigen not found on LB33-MEL.A.

Figure 10A:
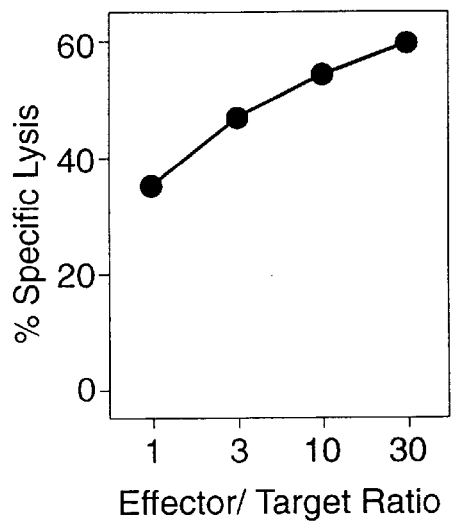

The experiments described herein parallel those described supra and, as in the prior experiments, another panel of CD8+ CTL clones were established. The panel of reactivity of CTL 269/1 is shown in FIG. 10A. Note reaction with "MEL.B-1", but not "MEL.A-1". The new antigen defined thereby is referred to as LB33-E.

Figure 10B:
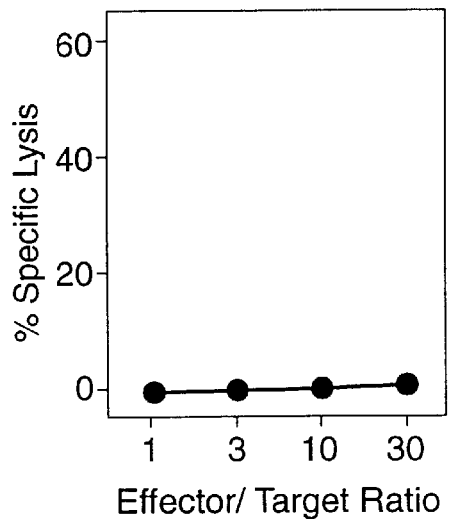
Figure 10C:
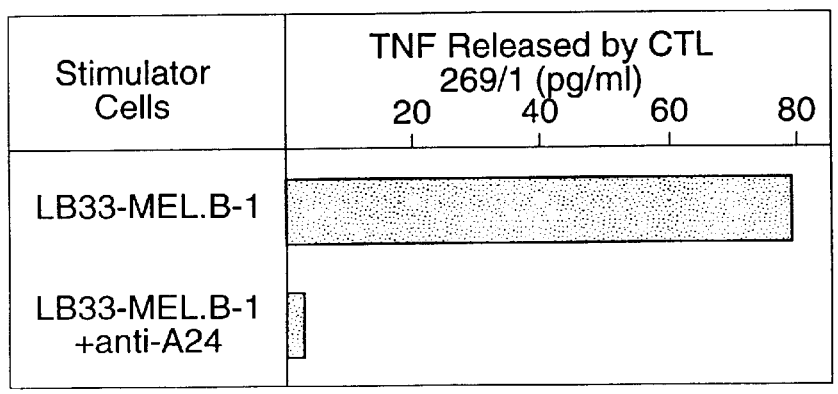

In antibody inhibitory experiments, mAbs to HLA-A24 inhibited lysis. This is shown in FIG. 10B. Hence, the "E" antigen is presented by HLA-A24.

EXAMPLE 13

Fleischhauer et al., Tissue Antigens 44: 311–317 (1994), incorporated by reference, teach a consensus motif for HLA-B44 binding. This motif is described as a nine or ten amino acid polypeptide, where Glu predominates at second position, Tyr or Phe is present at the last position (position 9 or 10), and hydrophobic residues, such as Met, are at the third position.

The MAGE-3 TRAP amino acid sequence contains a stretch of amino acids at position 167–176, which corresponds to this motif. The amino acid sequence is:

Met Glu Val Asp Pro Ile Gly His Leu Tyr (SEQ ID NO: 17).

The HLA-B44 motif is known to contain at least two major subtypes, referred to as HLA-B* 4402 and HLA-B* 4403. The MHC molecule appears on 23% of all Caucasians. When this figure is combined with standard analyses of melanoma, it is concluded that 15% of Caucasian melanoma patients should present HLA-B44 on the surface of their melanoma cells. Thus, it is of great interest to determine if the peptide of SEQ ID NO: 17 or related molecules can in fact be used to identify HLA-B44 cells, and to provoke their lysis following binding to the MHC molecule. As noted in prior examples, the peptide of SEQ ID NO: 2 was shown to bind to HLA-B44 positive cells. A peptide was designed with was similar to SEQ ID NO: 2, except for having Ala at position 8, rather than Leu. This new peptide, i.e.:

Glu Glu Lys Leu Ile Val Val Ala Phe (SEQ ID NO: 18), was tested in a competition assay with SEQ ID NO: 17. This peptide was used in view of result obtained in experiments not reported here. Briefly, derivatives of SEQ ID NO:17 were prepared, wherein each derivative contained an Ala at a position not occupied by Ala in SEQ ID NO:17. CTL clone 159/5 was slightly better at recognizing complexes containing SEQ ID NO:18 than SEQ ID NO:17, making it an excellent reagent for competitive assays. Competition was carried out using C1R cells, described by Storkus et al., J. Immunol 138:1657–1659 (1987). These C1R cells are MHC class I negative, lymphoblastoid cells. The C1R cells were transfected with cDNA for HLA-B*4402, or genomic DNA HLA-B*4403, using the same methodology given supra. The cDNA for HLA-B*4402 is set forth by Fleischhauer, et al, Tissue Antigens 44: 311–317 (1994), while that for HLA-B*4403 is given by Fleischhauer, et al. (1990) New Eng. J. Med 323:1818–1822 (1990). Both papers are incorporated by reference.

The cells were labelled with $^{51}$Cr for one hour at 37° C., in the presence of anti-HLA class I monoclonal antibody W6/32 (30% (v/v) of culture medium of the hybridoma cells). This increases the ability of the cells to present antigenic peptides to T cells.

Labelled cells were washed, and incubated for 30 minutes at 20° C., in serum free medium, together with various concentrations of competitor peptides. These peptides included:

Ser Glu Ile Trp Arg Asp Ile Asp Phe (SEQ ID NO: 3) which binds to HLA-B44 molecules, as discussed, supra Phe Leu Arg Gly Arg Ala Tyr Gly Leu (SEQ ID NO: 19), which is encoded by EBV gene EBNA-3A and binds to HLA-B8 (Burrows, J. Exp Med 171:345–349 (1990)), and SEQ ID NO: 17.

The peptide of SEQ ID NO: 18 was then added in the serum free culture medium at a final concentration of 45 ng/ml, (C1R-B4402$^+$ cells), or 160 ng/ml (C1R-B4403$^+$ cells). The cells were incubated for 30 minutes at 20 C, and washed twice in Iscove's medium plus 2% fetal calf serum. The CTL clone LB33-CTL 159/5 was added in Iscove's medium and 10% human serum, at an E:T ratio of 20. The release of $^{51}$Cr was measured after three hours, and is shown in FIGS. 11A and 11B, for C1R-B*4402 and C1R-B*4403 cells. The data presented in FIG. 11, show clear evidence of competition.

EXAMPLE 14

Additional experiments were then carried out following those described in Example 13.

Cytolytic T cell clones (CTLs) were derived from two subjects, referred to as LB 816 and LB 822, respectively. These subjects showed no evidence of cancer.

Blood mononuclear cells (BMCs) were isolated from the subjects, using density gradient centrifugation. T lymphocytes in the BMCs were purified by resetting, using sheep red blood cells which had been treated with aminoethyl-isothiouronium bromide, and then labelled with an anti-CD8 monoclonal antibody coupled to magnetic microbeads. The CD8$^+$ cells were sorted by passage through a magnetized area, and then stored at –80° C. in Iscove's culture medium, supplemented with 10% human serum, 116 mg/ml L-arginine, 36 mg/ml L-asparagine, and 216 mg/ml of L-glutamine, 0.05M 2-mercaptoethanol, and 10% DMSO.

Any non-rosetting BMCS were left to adhere for two hours at 37° C. on tissue culture plates. Non-adherent cells were discarded, and adherent cells cultured for seven days in the presence of IL-4 (50 U/ml), and GM-CSF (100 ng/ml). The resulting population was enriched for antigen presenting cells ("APCs"; in this case, dendritic cells or macrophages). Then, from 5×10$^5$ to 10$^6$ of these cells were incubated in 2 ml wells for four hours, at 37° C., in 400 ul Iscove's medium supplemented with 2.5 ug/ml of human B2 microglobulin, and 50 ug/ml of the peptide of SEQ ID NO: 17. Adherent, peptide pulsed cells were then irradiated at 5000 rads, and washed. Next, 2×10$^6$ autologous CD8$^+$ T cells were added, in culture medium, supplemented with 1000 U/ml of IL-6, and 5 ng/ml of IL-12.

Seven days later, lymphocytes were restimulated with adherent, autologous BMCs, pulsed with peptide as above. 5×10$^6$ BMCs were left to adhere for two hours at 37° C., in 400 ul Iscove's medium containing B2-microglobulin and SEQ ID NO: 17, as discussed above. Any peptide pulsed, adherent cells, were irradiated and washed. Responder cells were then added, in culture medium supplemented with 10 U/ml of IL-2, and 5 ng/ml of IL-7.

On day 14, the lymphocytes were restimulated with autologous BMCs pulsed with SEQ ID NO: 17. The BMCs were incubated, at 2×10$^7$ cells/ml, in the augmented Iscove's medium discussed supra but without 10% DMSO. After two hours of incubation (20° C.), peptide pulsed BMCs were irradiated, washed, and resuspended at 2×10$^6$ cells /ml in culture medium augmented with IL-2 and IL-7, as above. Samples of these stimulator cells (2×10$^6$), were added to each well which contained responder cells.

The responder lymphocytes were cloned on day 21. Anywhere from 10 to 0.3 cells/well were seeded in microwells, in culture medium which had been supplemented with 50 U/ml of IL-2, and 5 U/ml of IL-4. These were then stimulated by adding allogenic EBV transformed B cells (LG2-EBV) and irradiated at 10,000 rads, at 20,000 cells per well, one of (i) allogeneic EBV-transformed B cells, (ii) peptide pulsed HLA-B4402+ cells, or (iii) peptide pulsed HLA-B4403+ cells. For (ii) or (iii), irradiation was at 15,000 rads, at 8000 cells per well.

Microcultures were restimulated every week in the same way they were on the 21st day. The one change was that at days 28 and 35, 40,000 and 60,000 EBV-B cells respectively were added per well, as compared to 20,000 at day 21.

Between days 41 and 52, aliquots of the proliferating microcultures were transferred into V-bottom microwells, in order to test for lytic activity against HLA-B4402+ or HLA-B4403+ target cells, pulsed and not pulsed with SEQ ID NO: 17.

Any microcultures which showed anti-peptide lytic activity were restimulated with 5×10$^4$ irradiated, peptide pulsed B4402+ or B4403+ cells, plus 5×10$^5$ irradiated LG2-EBV-B cells, in 800 ul of culture medium augmented with 50 U/ml of IL-2, and 5 U/ml of IL-4.

After seven days, the CTL clones were restimulated every week with 2×10$^5$ irradiated peptide pulsed B4402+ or B4403+ cells, together with 10$^6$ irradiated LG2-EBV-B cells, as described supra. In this way, CTLs LB 816-CTL-340 A/1, and LB822-CTL-346A/1 were obtained. These CTLs are specific for complexes of SEQ ID NO: 17 and either HLA-B*4402, or HLA-B4403, respectively.

EXAMPLE 15

In a further set of experiments, HLA-B4402+ or HLA-B4403+ EBV transformed B cells which do not express MAGE-3 were labelled with $^{51}$Cr in the presence of monoclonal antibody W6/32, for 1 hour, at 37° C., following Brodsky, et al, J. Immunol 128:135 (1982). The cells were washed, and incubated for 30 minutes at 20° C. in serum free medium, using varied concentrations of SEQ ID NO: 17. Each CTL described in Example 14 was tested in a $^{53}$Cr release assay, also as described, with chromium release being measured after four hours.

Figure 12B:
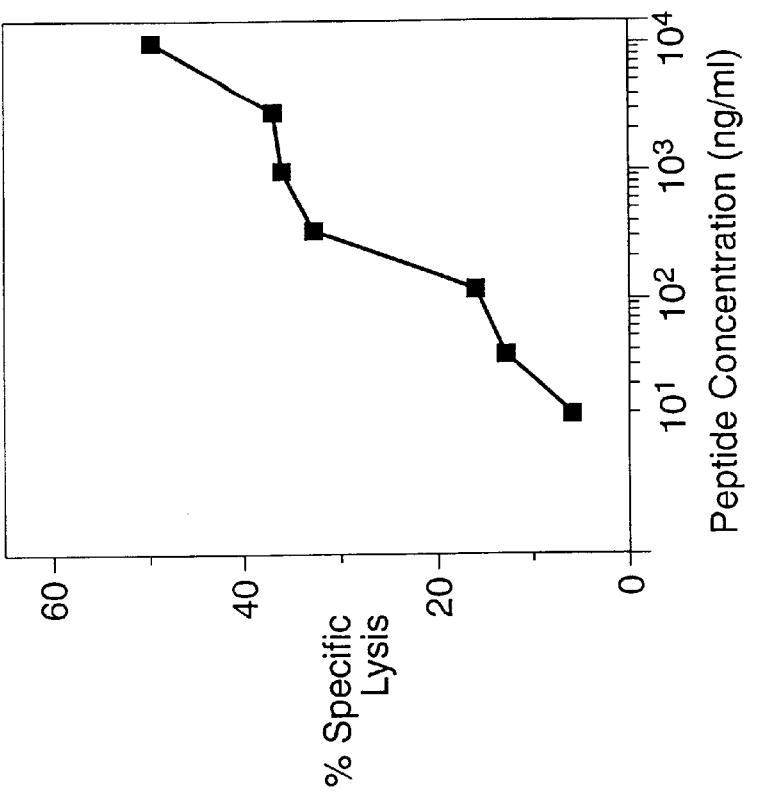
FIGS. 12A–12B depict the result obtained when SEQ ID NO: 17 was used in connection with cells which naturally present HLA-B44, in $^{51}$Cr release assays.
Figure 12A:
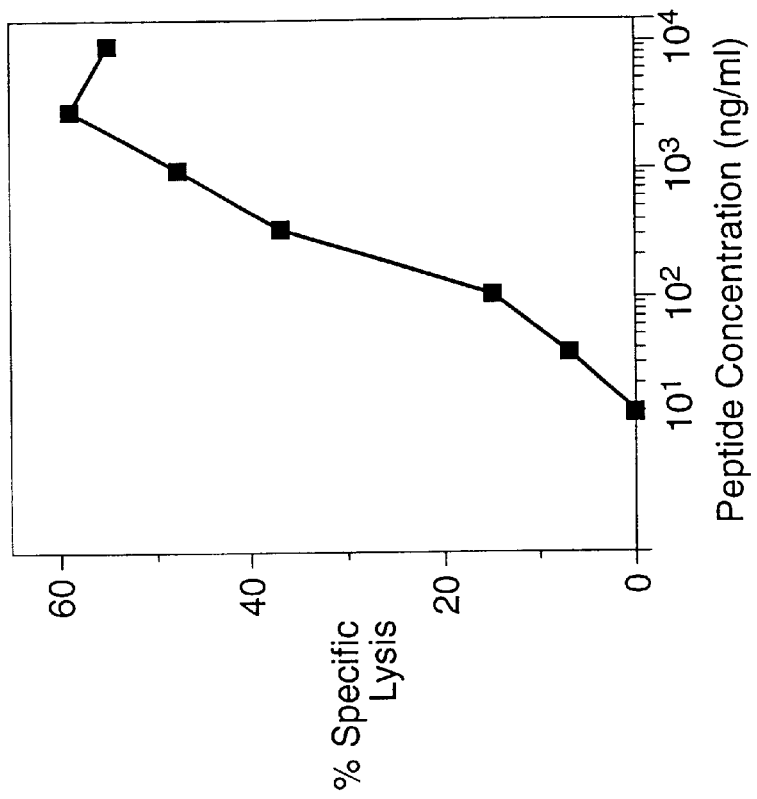

The results, set forth in FIG. 12, shows that the peptide did, in fact, provoke lysis.

EXAMPLE 16

In the following experiments, additional tumor cell lines which are HLA-B44 positive were examined.

Figures 13A, 13B:
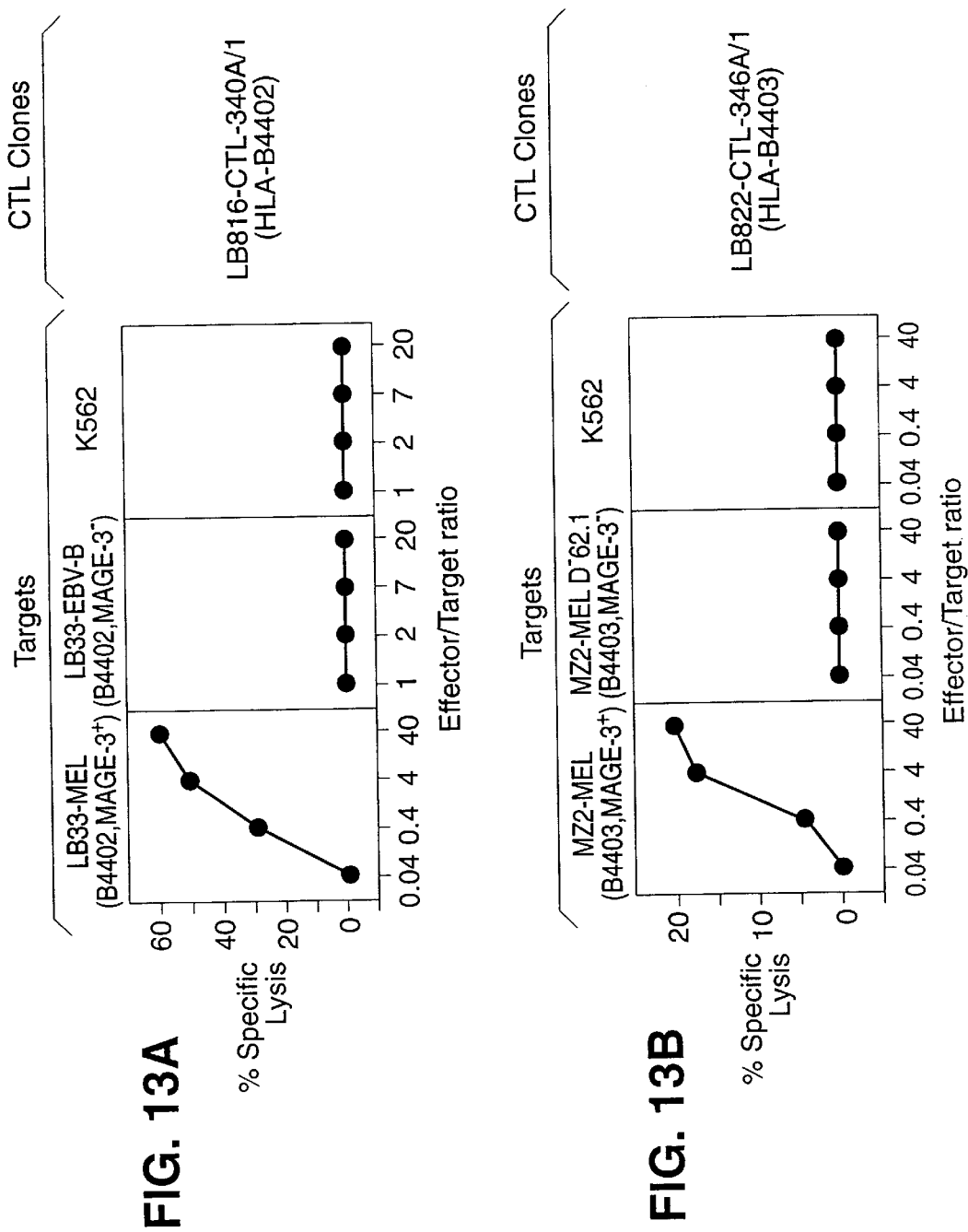
FIGS. 13A–13B summarize the results of $^{51}$Cr lysis assays where the target cells were naturally HLA-B44 positive, such as cancer cell lines.

All cell lines tested were labelled with $^{51}$Cr for one hour, at 37° C. They were then added in Iscove's medium plus 2% fetal calf serum, to various numbers of the two CTL clones discussed in example 14. The amount of $^{51}$Cr released was measured after four hours. Controls were also used, as indicated in FIG. 13. Note that the cell line LB33-MEL was incubated with IFN-γ (50 U/ml), for 48 hours before the assay.

The results of these experiments are shown in FIG. 13. CTL clones LB816-CTL-340 A/1 and LB822-CTL-346 A/1 lysed tumor cells expressing MAGE-3, but did not lyse LB33-EBv B cells which did not express the MAGE gene. The CTL clone LB822-346 A/1 lysed the HLA-B*4403+ tumor cell line MZ2-MEL, which expresses MAGE-3, but did not lyse the antigen loss variant MZ2-MEL.61.2D$^-$.

EXAMPLE 17

As a final test to determine if the peptide of SEQ ID NO: 17, in complexes with HLA-B44, stimulated CTLs, experiments were carried out to determine if tumor necrosis factor release was stimulated.

First, COS-7 cells were transfected by cDNA encoding MAGE-3 following Gaugler, et al, J. Exp. Med 179:921–930 (1994), in the expression vector PcDNA-I/AMP, and one of HLA-B*4402 cDNA cloned into vector pcDNA3, or HLA-B 4403 cDNA cloned into pcDNA1/AMP. The DEAE dextran chloroquine method of Aruffo, Proc. Natl. Acad. Sci. USA 84:3365–3369 (1987) was used.

Transfectants were incubated for 24 hours, at 37° C., then 3000 CTLs/well were added. Materials were incubated for 18 hours, at 37° C. Supernatants were then collected, and TNF content was determined by tested the cytolytic effect on TNF sensitive WEHI-16 clone 13 cells, following Espevik et al, J. Immunol. Meth 95:99–105 (1986).

Table 3, which follows, shows the results, wherein TNF release is expressed in pg/ml. LB33-MEL and LB494 MEL were incubated with IFNγ at 100 U/ml for 24 hours prior to the assay. Tumor Cell lines LB33-MEL, LB494-MEL, and MZ2-MEL were also tested. These cell lines all express MAGE-3 cDNA, and are either HLA-B*4402+ (LB33-MEL, LB494-MEL), or HLA-B*4403+ (MZ2-MEL). Hence, no transfection was necessary for these cells. The results show that TNF was released. Hence, one concludes that SEQ ID NO: 17 is being presented by HLA-B44 MHC molecules, and these complexes provoke CTL activity.

TABLE 3

TNF production of anti-MAGE–3.B44 CTL clones

| | CTL Clones | Stimulator cells | TNF (pg/ml) |
|---|---|---|---|
| A | LB816-CTL-340A/1 (B4402) | COS | 0.7 |
| | | COS+MAGE-3 | 0.6 |
| | | COS+HLA-B4402 | 0.5 |
| | | COS+HLA+B4402+MAGE-3 | 33.7 |
| | | LB33-MEL (B4402, MAGE-3+++) | 74.9 |
| | | LB494-MEL (B4402, MAGE-3+++) | 32.3 |
| B | LB822-CTL-346A/1 (B4403) | COS | 1.2 |
| | | COS+MAGE-3 | 1 |
| | | COS+HLA-B4403 | 1.2 |
| | | COS+HLA-B4403+MAGE-3 | 26.6 |
| | | MZ2-MEL (B4403, MAGE-3+++) | 67.3 |

The foregoing experiments describe isolated nucleic acid molecules coding for a tumor rejection antigen precursor, a "TRAP" molecule. The protein molecule for which these code is processed intracellularly in a manner which leads to production of at least one tumor rejection antigen, or "TRA", which is presented by HLA-B44 molecules. While it has been observed previously that HLA-B44 molecules present peptides derived from tyrosinase, the nucleic acid molecules of the invention do not code for tyrosinase, and the TRAs are not tyrosinase derived.

The tumor rejection antigens of the invention are isolated nonapeptides which have a Glu residue at the 2nd position, and a Phe or Tyr residue at the 9th or 10th position. Especially preferred are the nonamer of SEQ ID NO: 2, i.e.:

Glu Glu Lys Leu Ile Val Val Leu Phe as well as the nonamer

Glu Glu Lys Leu Ile Val Val Ala Phe (SEQ ID NO: 18) and the decamer:

Met Glu Val Asp Pro Ile Gly His Leu Tyr (SEQ ID NO: 17).

Also useful are nonapeptides which, in addition to the required residues at positions 2 and 9 or 10, have one or more These are set forth in SEQ ID NOS: 20, 21, 22, and 23 of the following defined residues:

position 1: Glu or Met
position 3: Lys or Val
position 4: Leu or Asp
position 5: Ile or Pro
position 6: Val or Ile
position 7: Val or Gly
position 8: Leu, Ala or His
position 9: Leu (when the peptide is a decamer)

Of particular interest are peptides which satisfy certain consensus motifs. These motifs include:

Xaa Glu (Xaa)$_3$ Val (Xaa)$_2$ Phe (SEQ ID NO:24)

and

Xaa Glu (Xaa), Val Xaa Phe (SEQ ID NO:25)

wherein Xaa is any amino acid, as well as the consensus motif

Xaa Glu (Xaa)$_{2,3}$ Ile (Xaa)$_3$ Xaa (SEQ ID NO:26 and 27) wherein the first, second, and third occurrences of Xaa refer to any amino acids, and the fourth one, i.e., the carboxy terminal amino acid, represents tyrosine or phenylalanine. Especially preferred are the peptides of SEQ ID NOS: 17 and 18, and the variations discussed, supra.

The peptides of the invention are similar to the peptide disclosed in Ser. No. 08/233,305 now U.S. Pat. No. 5,519,117, co-assigned to the assignee of the subject application, i.e.:

Ser Glu Ile Trp Arg Asp Ile Asp Phe (SEQ ID NO: 3)

Khanna, et al., supra, teaches a decamer, i.e.:

Glu Glu Asn Leu Leu Asp Phe Val Arg Phe (SEQ ID NO: 4)

but does not discuss how modification of the decamer could lead to an effective nonamer.

The invention thus involves tumor rejection antigens which bind to HLA-B44 molecules, and then provoke lysis by CTLs.

As indicated, the complexes of TRA and HLA molecule provoke a cytolytic T cell response, and as such isolated complexes of the tumor rejection antigen and an HLA-B44 molecule are also encompassed by the invention, as are isolated tumor rejection antigen precursors coded for by the previously described nucleic acid molecules. Given the binding specificity, the peptides may also be used, simply to identify HLA-B44 positive cells.

The invention as described herein has a number of uses, some of which are described herein. First, the identification of a tumor rejection antigen which is specifically presented by an HLA-B44 molecule, as well as a nucleic acid molecule coding for its parallel tumor rejection antigen precursor permits the artisan to diagnose a disorder characterized by expression of the TRAP. These methods involve determining expression of the TRAP gene, and/or TRAs derived therefrom, such as TRA presented by HLA molecules. Other TRAs may also be derived from the TRAPs of the invention and presented by different HLA molecules. In the former situation, such determinations can be carried out via any standard nucleic acid determination assay, including the polymerase chain reaction, or assaying with labelled hybridization probes. In the latter situation, assaying with binding partners for complexes of TRA and HLA, such as antibodies, is especially preferred.

The isolation of the TRAP gene also makes it possible to isolate the TRAP molecule itself, especially TRAP molecules containing the amino acid sequence of SEQ ID NO: 1. Fragments of peptides of these isolated molecules when presented as the TRA, or as complexes of TRA and HLA, B44, may be combined with materials such as adjuvants to produce vaccines useful in treating disorders characterized by expression of the TRAP molecule. In addition, vaccines can be prepared from cells which present the TRA/HLA complexes on their surface, such as non-proliferative cancer cells, non-proliferative transfectants, etcetera. In all cases where cells are used as a vaccine, these can be cells transfected with coding sequences for one or both of the components necessary to prove a CTL response, or be cells which express both molecules without transfection. Further, the TRAP molecule, its associated TRAs, as well as complexes of TRA and HLA, may be used to produce antibodies, using standard techniques well known to the art.

When "disorder" is used herein, it refers to any pathological condition where the tumor rejection antigen precursor is expressed. An example of such a disorder is cancer, melanoma in particular.

Therapeutic approaches based upon the disclosure are premised on a response by a subject's immune system, leading to lysis of TRA presenting cells, such as cells presenting the relevant HLA molecule. One such approach is the administration of CTLs specific to the complex to a subject with abnormal cells of the phenotype at issue. it is within the skill of the artisan to develop such CTLs in vitro. Specifically, a sample of cells, such as blood cells, are contacted to a cell presenting the complex and capable of provoking a specific CTL to proliferate. The target cell can be a transfectant, such as a COS cell of the type described supra. These transfectants present the desired complex on their surface and, when combined with a CTL of interest, stimulate its proliferation. COS cells, such as those used herein are widely available, as are other suitable host cells.

To detail the therapeutic methodology, referred to as adoptive transfer (Greenberg, J. Immunol. 136(5): 1917 (1986); Reddel et al., Science 257: 238 (7-10-92); Lynch et al., Eur. J. Immunol. 21: 1403–1410 (1991); Kast et al., Cell 59: 603–614 (11-17-89)), cells presenting the desired complex are combined with CTLs leading to proliferation of the CTLs specific thereto. The proliferated CTLs are then administered to a subject with a cellular abnormality which is characterized by certain of the abnormal cells presenting the particular complex. The CTLs then lyse the abnormal cells, thereby achieving the desired therapeutic goal.

The foregoing therapy assumes that at least some of the subject's abnormal cells present the HLA/TRA complex. This can be determined very easily, as the art is very familiar with methods for identifying cells which present a particular HLA molecule, as well as how to identify cells expressing DNA containing the indicated sequences. Once isolated, such cells can be used with a sample of a subject's abnormal cells to determine lysis in vitro. If lysis is observed, then the use of specific CTLs in such a therapy may alleviate the condition associated with the abnormal cells. A less involved methodology examines the abnormal cells for HLA phenotyping, using standard assays, and determines expression via amplification using, e.g., PCR.

Adoptive transfer is not the only form of therapy that is available in accordance with the invention. CTLs can also be provoked in vivo, using a number of approaches. One approach, i.e., the use of non-proliferative cells expressing the complex, has been elaborated upon supra. The cells used in this approach may be those that normally express the complex, such as irradiated melanoma cells or cells transfected with one or both of the genes necessary for presentation of the complex. Chen et al., Proc. Natl. Acad. Sci. USA 88: 110–114 (January, 1991) exemplifies this approach, showing the use of transfected cells expressing HPVE7 peptides in a therapeutic regime. Various cell types may be used. Similarly, vectors carrying one or both of the genes of interest may be used. Viral or bacterial vectors are especially preferred. In these systems, the gene of interest is carried by, e.g., a *Vaccinia* virus or the bacteria BCG, and the materials de facto "infect" host cells. The cells which result present the complex of interest, and are recognized by autologous CTLs, which then proliferate. A similar effect can be achieved by combining the tumor rejection antigen or the precursor itself with an adjuvant to facilitate incorporation into cells which present the HLA molecule of interest. The TRAP is processed to yield the peptide partner of the HLA molecule while the TRA is presented without the need for further processing.

Other aspects of the invention will be clear to the skilled artisan and need not be repeated here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. Isolated peptide consisting of the amino acid sequence set forth in SEQ ID NO: 17.

2. Method for identifying an HLA-B44 positive cell in a sample comprising contacting said sample with the isolated peptide of claim 1 and determining binding of said peptide as a determination of HLA-B44 positive cells in said sample.

* * * * *